United States Patent [19]
Hellstrom et al.

[11] Patent Number: 5,491,088
[45] Date of Patent: Feb. 13, 1996

[54] MONOCLONAL ANTIBODY BR 96 AND CHIMERIC MONOCLONAL ANTIBODIES HAVING THE VARIABLE REGION OF MAB BR96, WHICH BIND TO A VARIANT OF LEY ANTIGEN ON HUMAN CARCIMONA CELLS

[75] Inventors: Ingegerd Hellstrom; Karl E. Hellstrom; Kim F. Bruce, all of Seattle; George J. Schreiber, Redmond, all of Wash.

[73] Assignee: Oncogen Limited Partnership

[21] Appl. No.: 57,444

[22] Filed: May 5, 1993

Related U.S. Application Data

[63] Continuation of Ser. No. 544,246, Jun. 26, 1990, abandoned, which is a continuation-in-part of Ser. No. 374,947, Jun. 30, 1989, abandoned.

[51] Int. Cl.$^6$ .............................. C12N 5/20; C07K 16/30
[52] U.S. Cl. .................. 435/240.24; 530/387.3; 530/387.5; 530/388.8; 435/172.2; 435/70.21; 435/240.2
[58] Field of Search .......................... 530/387.3, 387.5, 530/388.85, 388.8; 435/240.27, 70.21, 172.2

[56] References Cited

U.S. PATENT DOCUMENTS

| | | |
|---|---|---|
| 4,474,893 | 10/1984 | Reading . |
| 4,507,391 | 3/1985 | Pukel et al. . |
| 4,579,827 | 4/1986 | Sakamoto et al. . |
| 4,612,282 | 9/1986 | Schlom et al. . |
| 4,676,980 | 6/1987 | Segal . |
| 4,708,930 | 11/1987 | Kortright et al. . |
| 4,713,351 | 12/1987 | Knauf . |
| 4,713,352 | 12/1987 | Bander et al. . |
| 4,737,579 | 4/1988 | Hellstrom et al. . |
| 4,753,894 | 6/1988 | Frankel et al. . |

FOREIGN PATENT DOCUMENTS

| | | |
|---|---|---|
| 8601533 | 3/1986 | WIPO . |
| 8905309 | 6/1989 | WIPO . |

OTHER PUBLICATIONS

Drebin et al. Oncogene 2: 273–277 1988.
Kannagi et al. "Handbook of Experimental Immunology vol. 4, Blackwell Sci Publ.," 1986, pp. 117.1–117.20.
Waldmann, Science 252:1657–1662 1991.
Carney et al. "Genes and Cancer" J. Wiley & Sons, 1990.
Dillman, Annals of Internal Medicine 111:592–603, 1989.
Harlow et al., "Antibodies A Laboratory Manual", CSH Laboratory, 1988, p. 287.
Thorpe, Monoclonal Antibodies '84: Biological and Clinical Applications, Rinchera et al. Eds., Editrice Kurtis, Publ 1985 pp. 475–506.
Hellstrom et al., "Antitumor effects of L6, and IgG2a antibody that reacts with most human carcinomas", Proc. Natl. Acad. Sci. USA, 83:7059–7063 (1986).
Drebin et al., "Monoclonal antibodies specific for the neu oncogene product directly mediate anti–tumor effects in vivo" Oncogene 2:387–394 (1988).
Papsidero, "Recent Progress in the Immunological Monitoring of Carcinomas Using Monoclonal Antibodies" Sem. in Surg. Onc. 1:171–181 (1985).
Schlom and Weeks, "Potential Clinical Utility of Monoclonal Antibodies in the Management of Human Carcinomas" Important Adv. Oncol., 170–92 (1985).
Allum et al., "Monoclonal Antibodies in the Diagnosis and Treatment of Malignant Conditions" Surg. Ann., 18:41–64 (1986).
Houghton and Scheinberg, "Monoclonal Antibodies: Potentail Applications to the Treatment of Cancer" Semin. Oncol., 13(2):165–79 (1986).
Fink and Clarke, "Monoclonal Antibodies as Diagnostic Reagents for the Identification and Characterization of Human Tumor Antigens" Prog. Clin. Pathol. 9:121–33 (1984).
Johnston, "Applications of Monoclonal Antibodies in Clinical Cytology as Exemplified by Studies with Monoclonal Antibody B72.3", Acta. Cytol., 1(5): 537–56 (1987).
Young et al., "Production of monoclonal antibodies specific for two distinct steric portions of the glycolipid anglio–N–tiosylcaramide" (Asialo $GM_2$) J. Exp. Med., 150:1008–1019 (1979).
Kniep et al., "Gangliotriaoslyceramide (Asialo $GM_2$) A glycosphingolipid marker for cell lines derived from patients with Hodgkin's disease" J. Immunol., 131: 1591–1594 (1983).
Rosen et al., "Analysis of Human Small Cell Lung Cancer Differentiation Antigens Using a Panel of Rat Monoclonal Antibodies" Cancer Res. 44:1052–2061 (1984).
Varki et al., "Antigens associated with a Human Lung Adenocarcinoma Defined by Monoclonal Antibodies"]Cancer Res., 44:681–687 (1984).
Embleton and Garnett, "Antibody Targeting of Anti–Cancer Agents", in Monoclonal Antibodies for Cancer Detection and Therapy, pp. 317–44, Academic Press (1985).
Domingo and Trowbridge, "Transferrin Receptor as a Target for Antibody–Drug Conjugates", Methods Enzymol., 112:238–47 (1985).
Kohler and Milstein, "Continuous cultures of fused cells secreting antibody of predefined specificity" Nature (London) 256:495 (1975).

(List continued on next page.)

Primary Examiner—Paula K. Hutzell
Attorney, Agent, or Firm—Merchant, Gould, Smith, Edell, Welter, & Schmidt

[57] ABSTRACT

The present invention relates to novel antibodies reactive with human carcinoma cells. More particularly, the antibodies of the invention include: a murine monoclonal antibody, BR96; a human/murine chimeric antibody, ChiBR96; and a F(ab')$_2$ fragment of BR96. These antibodies are reactive with a cell membrane antigen on the surface of human carcinomas. The antibodies display a high degree of selectivity for carcinoma cells and possess the ability to mediate ADCC and CDC activity. In addition, the antibodies of the invention internalize within the carcinoma cells to which they bind. The antibodies also have a unique feature in that they are cytotoxic when used in the unmodified form, at specified concentrations.

12 Claims, 27 Drawing Sheets

OTHER PUBLICATIONS

Oi et al., *Proc. Natl. Acad. Sci USA* 80:825 (1983), "Immunoglobulin gene expression in transformed lymphoid cells".

Potter et al., *Proc. Natl. Acad. Sci USA*, 81:7161, "Enhancer–dependent expression of human K immunoglobulin genes introduced into mouse pre–B lymphocytes by electroporation".

Morrison et al., *Proc. Natl. Acad. Sci USA*, 81:6581 (1984), "Chimeric human antibody molecules: Mouse antigen–binding domains with human constant region domains".

Sahagan et al., *J. Immunol.*, 137:1066 (1986), "A Genetically Engineered Murine/Human Antibody Retains Specificity for Human Tumor–Associated Antigen".

Sun et al., "Proc. Natl. Acad. Sci., 84:214 (1987), Chimeric antibody with human constant regions and mouse variable regions directed against carcinoma–associated antigen 17–1A".

Boulianne et al., *Nature*, 312:643 (1984), "Production fo functional chimaeric mouse/human antibody".

Sharon et al., *Nature*, 309:364 (1984), "Expression of a $V_H C_K$ chimeric protein in mouse myeloma cells".

Tan et al., *J. Immunol.*, 135:3565–3567 (1985), "A human–mouse chimeric immunoglobulin gene with a human variable region is expressed in mouse myeloma cells".

Folger et al., *Symp. Quant. Biol.*, 49:123–138 (1984), "Analysis of Homologous Recombination in Cultured Mammalian Cells".

Folger et al., *Mol. Cell Biol.* 2:1372–1387 (1982), "Patterns of Integration of DNA Microinjected into Cultured Mammalian Cells: Evidence for Homologous Recombination Between Injected Plasmid DNA Molecules".

Kucherlapati, *Proc. Natl. Acad. Sci. USA* 81:3153–3157 (1984), "Homologous recombination between plasmids in mammalian cells can be enhanced by treatment of input DNA".

Lin et al., *Proc. Natl. Acad. Sci USA*, 82:1391–1395 (1985), "Recomination in mouse L Cells between DNA introduced into cells and homologous chromosomal sequences".

de Saint Vincent et al., *Proc. Natl. Acad. Sci. USA*, 80:2002–2006 (1983), "Homologous recombination in mammalian cells mediates formation of a functional gene from two overlapping gene fragments".

Shaul et al., *Proc. Natl. Acad. Sci. USA* 82:3781–3784 (1985), "Homologous recombination between a defective virus and a chromosomal sequence in mammalian cells".

Thomas et al., *Cell*, 44:419–428 (1986), "High Frequency Targeting of Genes to Specific Sites in the Mammalian Genome".

Smithies et al., *Nature*, 317:230–234 (1985), "Insertion of DNA sequences into the human chromosomal B–globin locus by homologous recombination".

Smith et al., *Symp. Quant. Biol.*, 49:171–181 (1984), "Homologous Recombination between Defective neo Genes in Mouse 3T6 Cells".

Song et al., *Proc. Natl. Acad. Sci USA*, 84:6820–6824 (1987).

Rubinitz and Subramani, *Mol. Cell Biol.*, 6:1608–1614 (1986), "Extrachromosomal and Chromosomal Gene Conversion in Mammalian Cells".

Liskay, *Cell*, 35:157–164 (1983), "Evidence for Intrachromosomal Gene Conversion in Cultured Mouse Cells".

Fell et al., "Homologous recombination in hybridoma cells: Heavy chain chimeric antibody produced by gene targeting", *Proc. Natl. Acad. Sci. USA*, 86:8507–8511.

Hellstrom et al., "Immunological Approaches to Tumor Therapy: Monoclonal Antibodies, Tumor Vaccines, and Anti–Idiotypes" in Covalently Modified Antigens and Antibodies in Diagnosis and Therapy, Quash, Rodwell, (Eds.) Marcel Dekker, Inc. (Publ.) (1988) pp.

Hellstrom et al., *Proc. Natl. Acad. Sci. USA*, 82:1499–1502 (1985), "Strong antitumor activities of IgG3 antibodies to a human melanoma–associated ganglioside".

Nudelman et al., "Characterization of a Human Melanoma–associated Ganglioside Antigen Defined by a Monoclonal Antibody, 4.2", *J. Biolog. Chemistry* 257(1):12752–56 (1982).

Hakamori, "Tumor–Associated Carbohydrate Antigens", *Ann. Rev. Immunol.*, 2:103–26 (1984).

Abe et al., "The Monoclonal Antibody Directed to Difucosylated Type 2 Chain (Fuc 1–2Gal 1–4 Fuc 1–3 GlycNAc; Y Determinant)", *J. Biol. Chem.*, 258:8934 (1983).

Lloyd et al., "Mouse Monoclonal Antibody F–3 Recognizes the Difocosyl Type–2 Blood Group Structure", *Immunogenetics*, 17:537 (1983).

Brown et al., "A monoclonal antibody against human colonic adenoma recognizes difucosylated Type–2–blood–groups chains", *Biosci. Reports* 3:163 (1983).

Hellstrom et al., "Monoclonal Mouse Antibodies Raised Against Human Lung Carcinoma", Cancer Res., 46:3917 (1986).

Abe et al., "Differential Expression of Difucosyl Type 2 Chain ($Le^Y$) Defined by Monoclonal Angibody AH6 in Different Locations of Colonic Eipthelia, Various Histological Types of Colonic Polyps and Adenocarcinomas", *Cancer Res.*, 46:2639–2644 (1986).

Brown et al., "Structural Characterization of Human Melanoma–Associated Antigen p97 with Monoclonal Antibodies", *J. Immunol.*, 127(2):539–46 (1981).

Brown et al., "Protein Antigens of Normal and Malignant Human Cells Identified by Immunoprecipitation with Monoclonal Antibodies", *J. Biol. Chem.*, 255:4980–83 (1980).

Yeh et al., "Cell surface antigens of human melanoma identified by monoclonal antibody", *Proc. Natl. Acad. Sci USA*, 76(6):297–31 (1979).

Yeh et al., "A Cell–surface antigen which is present in the ganglioside fraction and shared by human melanomas", Int. J. Cancer. 29:269–75 (1982).

Zola et al., "Techniques For the Production and Characterization of Monoclonal Hybridoma Antibodies", in Monoclonal Hybridoma Antibodies: Techniques and Applications, Hurell (Ed.), pp. 51–52, CRC Press, (1982).

Rouseaux et al., "Optimal Conditions for the Preparation of Proteolytic Fragments from Monoclonal IgG of Different Rat IgG Subclasses" in *Methods Enzymol.*, 121:663–69 (Academic Press, (1986).

Bagshawe, "Tumour markers—Where do we go from here?", *Br. J. Cancer*, 48: 167–75 (1983).

Thammana et al., "Immunoglobulin Heavy Chain Class Switch from IgM to IgG in a Hybridoma"*Eur. J. Immunol.*, 13:614 (1983).

Spira et al., "The Identification of Monoclonal Class Switch Variants by Sub–selection and ELISA Assay", *J. Immunol. Meth.*, 74:307–15 (1984).

Neuberger et al., "Recombinant antibodies possessing novel effector functions" *Nature*, 312:604–608 (1984).

Oi, "Chimeric Antibodies", *Biotechniques* 4(3):214–21 (1986).

Nepom et al., "Anti–idotypic antibodies and the induction of specific tumor immunity", in Cancer and Metastasis Reviews, 6:487–501 (1987).

Ciocca et al., "Immunohistochemical Techniques Using Monoclonal Antibodies" *Meth. Enzymol.*, 121–562–79 (1986).

Kimball (Ed.), *Introduction to Immunology*, (2nd Ed.), pp. 113–117 (Macmillan Publ. co.) (1986).

Uotila et al., "Two–site sandwich enzyme immunoassay with monoclonal antibodies to human alpha–fetoprotein" *J. Immunol. Methods*, 42:11 (1981).

Sikora et al., (Eds.), *Monoclonal Antibodies*, pp. 32–52 (Blackwell Scientific Publ., 1984).

Wensel and Meares, "'Bifunctional' Chelating Agents for Binding Metal Ions to Proteins" *Radioimmunoimaging and Radioimmunotherapy*, Esevier, N.Y. (1983).

Colcher et al., "Use of Monoclonal Antibodies as Radiopharmaceuticals for the Localization of Human Carcinoma Xenografts in Athymic Mice", *Meth. Enzymol.*, 121:802–16 (1986).

Bradwell et al., "Developments in Antibody Imaging", in *Monoclonal Antibodies for Cancer Detection and Therapy*, Baldwin et al., (Eds.), pp. 65–85, Academ. Press (1985).Arnon et al., "Monoclonal Antibodies for Immunotargeting of Drugs in Cancer Therapy" Reisfeld et al., (Eds.), pp. 243–256 (Alan R. Liss, Inc. 1985).

Hellstrom et al., "Antibodies for Drug Delivery" in *Controlled Drug Delivery* (2nd Ed.), Robinson et al., (Eds.) (Marcel Dekker Inc., 1987).

Thorpe et al., "The Preparation and Cytotoxic Properties of Antibody–Toxin Conjugates" *Immunol. Rev.*, 62:119–58 (1982).

Order, "Analysis, Results and Future Prospective of the Therapeutic Use of Radiolabeled Antibody in Cancer Therapy," in *Monoclonal Antibodies for Cancer Detection and Therapy* Baldwin (Eds) pp. 303–316, Academ. Press (1985).

Senter et al., "Anti–tumor effects of antibody–alkaline phosphatase conjugates in combination with etoposide phosphate", Proc. Natl. Acad. Sci. USA, 85:4842–4846 (1988).

Senter, "Enhancement of the in vitro and in vivo Antitumor Activities of Phosphorylated Mitomycin C and Etoposide Derivatives by Monoclonal Antibody–Alkaline Phosphates Conjugates" *Cancer Res.*, 49:5789–5792 (1989).

Senter, "Activation of Prodrugs by Antibody–Enzyme Conjugates: A New Approach to Cancer Therapy" *FASEB J.*, 4:188–193 (1990).

Ramsey et al., "Bone Marrow Purigng Using Monoclonal Antibodies", *J. Clinical Immunol.*, 8(2):81–88 (1988).

Kohler and Milstein, *Eur. J. Immunol.*, 6:511–19 (1976), "Derivation of specific antibody–producing tissue culture and tumor lines by cell fusion".

Douillard and Hoffman, "Enzyme–Linked Immunosorbent Assay for Screening Monoclonal Antibody Production Using Enzyme–Labeled Second Antibody" *Meth. Enzymol.*, 92:168–74 (1983).

Sternberger, "The Unlabeled Antibody Peroxidas–Antiperoxidase (PAP) Method" in Immunochemistry, pp. 104–169.

Garrigues et al., "Detection of a Human Melanoma–Associated Antigen, p. 97, in Histological Sections of Primary Human Malanomas", *Int. J. Cancer*, 29:511–15 (1982).

Hellstrom et al., "Monoclonal Antibodies to two Determinants of Melanoma–Antigen p. 97 Act Synergistically in Complement–Dependent Cytotoxicity", *J. Immunol.*, 127:157–60 (1981).

Brown et al., "Quantitative Analysis of Melanoma–Associated Antigen p. 9/in Normal and Neoplastic Tissues", *Proc. Natl. Acad. Sci. USA*, 78:539–43 (1981).

Blakey et al., "Effect of Chemical Deglycosylation of Ricin A Chain on the in vivo Fate and Cytotoxic Activity of An Immunotoxin Composed of Ricin A Chain and Anti–Thy 1.1 Antibody", *Cancer Res.*, 47:947–952 (1987).

Lambert et al., "Purified Immunotoxins That Are Reactive with Human Lymphoid Cells" *J. of Biolog. Chem.*, 260:12035–12041 (1985).

Knowles and Thorpe, "Purification of Immunotoxins Containing Ricin A–Chain and Abrin A–Chain Using Blue Sepharose CL–6B", *Analytic. Biochem.*, 160:440–443 (1987).

Krishan, "Rapid Flow Cytofluorometric Analysis of Mammalian Cell Cycle by Propidium Iodide Staining", *J. Cell. Biol.*, 66:188 (1975).

Yeh, *J. Immunol. Methods*, 43:269 (1981), "Propidium Iodide as a Nuclear Marker in Immunofluorescence. II. Use with Cellular Identification and Viability Studies".

Linsley et al., "Identification and Characterization of Cellular Receptors for Growth Regulator, Oncostatin M", *J. Biol. Chem.*, 264:4282–4289 (1989).

Cerotinni and Brunner, "Cell–Mediated Cytotoxicity, Allograft Rejection, and Tumor Immunity", *Adv. Immunol.*, 18:67–132 (1974).

Hellstrom et al., *Int. J. Cancer*, 27:281–285 (1981), "Lymphocyte–Dependent Antibodies to Antigen 3.1. A Cell–Surface Antigen Expressed by a Subgroup of Human Malanomas".

Hellstrom et al., "Antibody–Dependent Cellular Cytotoxicity to Human Melanoma Antigens", in *Monoclonal Antibodies and Cancer Therapy*, UCLA Symposia on Molecular and Cellular Biology, Reisfeld (ED), Liss, New York, vol. 27, pp. 149–164 (1985).

Lamoyi, "Preparation of F(ab')$_2$ Fragments from Mouse IgG of Various Subclasses" Meth. Enzymol., 121:652–663 (1986).

Hellstrom et al., *Cancer Res.*, 50:2449–2454 (1990), "Epitope Mapping and Use of Anti–Idiotypic Antibodies to the L6 Monoclonal Anticarcinoma Antibody".

Coffino et al., "Cloning of Mouse Myeloma Cells and Detection of Rare Variants" J. Cell Physiol., 79:(3)429–440 (1972).

Brennan et al., "Preparation of Bispecific Antibodies by Cheimical Recombination of Monoclonal Immunoglobulin $G_1$ Fragments", Science, 229:(05):81–83 (1985).

Bara et al., "Ectopic Expression of the Y (Le) Antigen Defined by Monoclonal Antibody 12–4LE in Distal Colonic Adenocarcinomas", *Int. J. Cancer*, 41:583–689 (1988).

Brady et al., "Therapeutic and Diagnostic Uses of Modified Monoclonal Antibodies" *I.J. Radiation Oncology Biol. Phys.* 13(10) (1987).

Drebin et al., "Down–Modulation of an Oncogene Protein Product and Reversion of the Transformed Phenotype by Monoclonal Antibodies", Cell 41:695–706 (1985).

Drebin et al., "Inhibition of tumor growth by a monoclonal antibody reactive with an oncogene–encoded tumore antigen", *Proc. Natl. Acad. Sci. USA*, 83:9129–9133 (1986).

Coding in *Monoclonal Antibodies: Priciniples and Practices*, pp. 118–125, Academic Press Inc. London (1983).

Hellstrom et al., "Highly Tumor–reactive, Internalizing, Mouse Monoclonal Antibodies to Le —related Cell Surface Antigens", *Cancer Res.* 50:2183–2190 (1990).

Kannagi et al., "New Globoseries Glycosphingolipids in Human Teratocarinoma Reactive with the Monoclonal Antibody Directed to a Developmentally Regulated Antigen, Stage–specific Embryonic Antigen 3", *J. Biol. Chem.,* 258(14):8934–8942 (1983).

Kim et al., "Expression of Le and Extended Le Blood Group–Related Antigens in Human Malignant, Premalignant and Nonmalignant Colonic Tissues", *Cancer Res.* 46: 5985–5992 (1986).

Morrison, "Transfectomas Provide Novel Chimeric Antibodies", *Science* 229:1202–1207 (1985).

FIG. 3

MONOCLONAL ANTIBODY BR 96 AND CHIMERIC MONOCLONAL ANTIBODIES HAVING THE VARIABLE REGION OF MAB BR96, WHICH BIND TO A VARIANT OF LEY ANTIGEN ON HUMAN CARCIMONA CELLS

CROSS-REFERENCE TO RELATED APPLICATIONS

This application is file wrapper continuation application of U.S. Ser. No. 07/544,246, filed Jun. 26, 1990, now abandoned, which was a continuation-in-part of U.S. Ser. No. 07/374,947, filed Jun. 30, 1989, now abandoned, the disclosure of which are incorporated by reference in its entirety herein.

TECHNICAL FIELD OF THE INVENTION

The present invention relates to novel antibodies reactive with human carcinoma cells. More particularly, the invention relates to a murine monoclonal antibody and a chimeric monoclonal antibody that react with a cell membrane antigen associated with a large variety of human carcinomas including carcinomas of the colon, breast, ovary and lung. The murine monoclonal antibody is highly specific for carcinomas, showing none to very low reactivity with normal human tissues or other types of tumors such as lymphomas or sarcomas. The antibodies of the invention have several added advantages. First, they internalize within the carcinoma cells to which they bind. The BR96 antibodies of the invention are therefore useful for therapeutic applications, for example, as the antibody component of antibody-drug or antibody-toxin conjugates where internalization of the conjugate is desired. Second, the antibodies mediate antibody-dependent cellular cytotoxicity "ADCC", and complement-mediated cytotoxicity, "CDC". Third, the antibodies can kill antigen-positive tumor cells in the unconjugated form if present at a sufficient concentration. The antibodies are also useful in diagnostic methods, such as the detection of carcinomas by in vitro or in vivo technology.

BACKGROUND OF THE INVENTION

Monoclonal antibodies to human tumor-associated differentiation antigens offer promises for the "targeting" of various antitumor agents such as radioisotopes, chemotherapeutic drugs, and toxins. [Order Baldwin and Byers, (eds.), in "Monoclonal Antibodies for Cancer Detection and Therapy", London, Academic Press (1985)]. In addition, some monoclonal antibodies have the advantage of killing tumor cells via ADCC or CDC in the presence of human effector cells or serum [Hellstrom et al., Proc. Natl. Acad. Sci. USA 83:7059–7063 (1986)], and there are a few monoclonal antibodies that have a direct antitumor activity which does not depend on any host component [Drebin et al., Oncogene 2:387–394 (1988)].

Many monoclonal antibodies reactive with carcinomaassociated antigens are known [see, e.g., Papsidero, "Recent Progress In The Immunological Monitoring Of Carcinomas Using Monoclonal Antibodies, Semin. Surg. Oncol., 1 (4):171–81 (1985); Schlom et al., "Potential Clinical Utility Of Monoclonal Antibodies In The Management Of Human Carcinomas", Important Adv. Oncol., 170–92 (1985); Allum et al., "Monoclonal Antibodies In The Diagnosis And Treatment of Malignant Conditions", Surg. Ann., 18:41–64 (1986); and Houghton et al., "Monoclonal Antibodies: Potential Applications To The Treatment Of Cancer", Semin. Oncol., 13(2):165–79 (1986)].

These known monoclonal antibodies can bind to a variety of different carcinoma-associated antigens including glycoproteins, glycolipids and mucins [see, e.g., Fink et al., "Monoclonal Antibodies As Diagnostic Reagents for The Identification And Characterization Of Human Tumor Antigens", Prog. Clin. Pathol., 9:121–33 (1984)]. For example, monoclonal antibodies that bind to glycoprotein antigens on specific types of carcinomas include those described in U.S. Pat. 4,737,579 (monoclonal antibodies to non-small cell lung carcinomas), U.S. Pat. No. 4,753,894 (monoclonal antibodies to human breast cancer), U.S. Pat. No. 4,579,827 (monoclonal antibodies to human gastrointestinal cancer), and U.S. Pat. No. 4,713,352 (monoclonal antibodies to human renal carcinoma). Monoclonal antibody B72.3, which is one of the antibodies studied the most, recognizes a tumor-associated mucin antigen of greater than 1,000 kd molecular weight that is selectively expressed on a number of different carcinomas. Thus, B72.3 has been shown to react with 84% of breast carcinomas, 94% of colon carcinomas, 100% of ovarian carcinomas and 96% of non-small cell lung carcinomas [see Johnston, "Applications of Monoclonal Antibodies In Clinical Cytology As Exemplified By Studies With Monoclonal Antibody B72.3", Acta Cytol., 1(5): 537–56 (1987) and U.S. Pat. No. 4,612,282, issued to Schlom et al.]. Another patented monoclonal antibody, KC-4, [see U.S. Pat. No. 4,708,930], recognizes an approximately 400–500 kd protein antigen expressed on a number of carcinomas, such as colon, prostate, lung and breast carcinoma. It appears that neither the B72.3 nor KC-4 antibodies internalize within the carcinoma cells with which they react.

Monoclonal antibodies reactive with glycolipid antigens associated with tumor cells have been disclosed. For example, Young et al., "Production Of Monoclonal Antibodies Specific For Two Distinct Steric Portions Of The Glycolipid Ganglio-N-Triosylceramide (Asialo $GM_2$)", J. Exp. Med., 150: 1008–1019 (1979) disclose the production of two monoclonal antibodies specific for asialo $GM_2$, a cell surface glycosphingolipid antigen that was established as a marker for BALB/c V3T3 cells transformed by Kirsten murine sarcoma virus. See, also, Kniep et al., "Gangliotriaosylceramide (Asialo $GM_2$) A Glycosphingolipid Marker For Cell Lines Derived From Patients With Hodgkin's Disease", J. Immunol., 131(3): 1591–94 (1983) and U.S. Pat. No. 4,507,391 (monoclonal antibody to human melanoma).

Other monoclonal antibodies reactive with glycolipid antigens on carcinoma cells include those described by Rosen et al., "Analysis Of Human Small Cell Lung Cancer Differentiation Antigens Using A Panel Of Rat Monoclonal Antibodies", Cancer Research, 44:2052–61 (1984) (monoclonal antibodies to human small cell lung cancer), Varki et al., "Antigens Associated with a Human Lung Adenocarcinoma Defined by Monoclonal Antibodies", Cancer Research 44:681–87 (1984); (monoclonal antibodies to human adenocarcinomas of the lung, stomach and colon and melanoma), and U.S. Pat. No. 4,579,827 (monoclonal antibodies to human colon adenocarcinoma). See, also, Hellstrom et al., "Antitumor Effects Of L6, An IgG2a Antibody That Reacts With Most Human Carcinomas", Proc Natl Acad Sci, USA, 83:7059–63 (1986) which describes the L6 monoclonal antibody that recognizes a carbohydrate antigen expressed on the surface of human non-small cell lung carcinomas, breast carcinomas and colon carcinomas.

Additional monoclonal antibodies exhibiting a high specific reactivity to the majority of cells from a wide range of carcinomas are greatly needed. This is so because of the antigenic heterogeneity of many carcinomas which often necessitates, in diagnosis or therapy, the use of a number of different monoclonal antibodies to the same tumor mass. There is a further need, especially for therapy, for so called "internalizing" antibodies, i.e., antibodies that are easily taken up by the tumor cells to which they bind. Antibodies of this type find use in therapeutic methods utilizing antibody-drug or antibody-toxin conjugates wherein a therapeutic antitumor agent is linked to an antibody for delivery to the tumor, where the antibody binds to the tumor-associated antigen with which it is reactive and "delivers" the antitumor agent inside the tumor cells [see, e.g., Embleton et al., "Antibody Targeting Of Anti-Cancer Agents", in *Monoclonal Antibodies For Cancer Detection and Therapy*, pp. 317–44 (Academic Press, 1985)]. Antibodies to tumor-associated antigens which are not able to internalize within the tumor cells to which they bind are generally not useful to prepare conjugates with antitumor drugs or toxins, since these would not be able to reach their site of action within the cell. Other approaches would then be needed so as to use such antibodies therapeutically.

Several internalizing antibodies reacting with lymphocyte antigens are known. In contrast, such antibodies are rare when dealing with solid tumors. One of the few examples of an internalizing antibody reacting with carcinomas is an antibody disclosed in Domingo et al., "Transferrin Receptor As A Target For Antibody-Drug Conjugates" *Methods Enzymol.* 112:238–47 (1985). This antibody is reactive with the human transferrin-receptor glycoprotein expressed on tumor cells. However, because the transferrin-receptor is also expressed on many normal tissues, and often at high levels, the use of an anti-transferrin-receptor antibody in a antibody-drug or antibody-toxin conjugate may have significant toxic effects on normal cells. The utility of this antibody for selective killing or inhibition of tumor cells is therefore questionable. Another internalizing antibody is BR64 (disclosed in patent applications U.S. Ser. No. 289,635, filed Dec. 22, 1988, (now abandoned), and Ser. No. 443,696 filed Nov. 29, 1989, (now U.S. Pat. No. 5,242,824), and incorporated by reference herein), which binds to a large spectrum of human carcinomas.

The cell fusion technique for the production of monoclonal antibodies [Kohler and Milstein, *Nature* (London) 256:495 (1975)] has permitted the development of a number of murine monoclonal antibodies reactive with antigens, including previously unknown antigens. Murine monoclonal antibodies, however, may be recognized as foreign substances by the human immune system and neutralized such that their potential in human therapy is not realized. Therefore, recent efforts have focused on the production of so-called "chimeric" antibodies by the introduction of DNA into mammalian cells to obtain expression of immunoglobulin genes [Oi et al., *Proc. Natl. Acad. Sci. USA* 80:825 (1983); Potter et al., *Proc. Natl. Acad. Sci. USA* 81:7161; Morrison et al., *Proc. Natl. Acad. Sci. USA* 81:6581 (1984); Sahagan et al., *J. Immunol.* 137:1066 (1986); Sun et al., *Proc. Natl. Acad. Sci.* 84:214 (1987)].

Chimeric antibodies are immunoglobulin molecules comprising a human and non-human portion. More specifically, the antigen combining region (variable region) of a chimeric antibody is derived from a non-human source (e.g. murine) and the constant region of the chimeric antibody which confers biological effector function to the immunoglobulin is derived from a human source. The chimeric antibody should have the antigen binding specificity of the non-human antibody molecule and the effector function conferred by the human antibody molecule.

In general, the procedures used to produce chimeric antibodies involve the following steps:

a) identifying and cloning the correct gene segment encoding the antigen binding portion of the antibody molecule; this gene segment (known as the VDJ, variable, diversity and joining regions for heavy chains or VJ, variable, joining regions for light chains or simply as the V or variable region) may be in either the cDNA or genomic form;

b) cloning the gene segments encoding the constant region or desired part thereof;

c) ligating the variable region with the constant region so that the complete chimeric antibody is encoded in a transcribable and translatable form;

d) ligating this construct into a vector containing a selectable marker and gene control regions such as promoters, enhancers and poly(A) addition signals;

e) amplifying this construct in bacteria;

f) introducing this DNA into eukaryotic cells (transfection) most often mammalian lymphocytes;

g) selecting for cells expressing the selectable marker;

h) screening for cells expressing the desired chimeric antibody; and k) testing the antibody for appropriate binding specificity and effector functions.

Antibodies of several distinct antigen binding specificities have been manipulated by these protocols to produce chimeric proteins [e.g. anti-TNP: Boulianne et al., *Nature* 312:643 (1984); and anti-tumor antigens: Sahagan et al., *J. Immunol.* 137:1066 (1986)]. Likewise, several different effector functions have been achieved by linking new sequences to those encoding the antigen binding region. Some of these include enzymes [Neuberger et al., *Nature* 312:604 (1984)], immunoglobulin constant regions from another species and constant regions of another immunoglobulin chain (Sharon et al., *Nature* 309:364 (1984); Tan et al., *J. Immunol.* 135:3565–3567 (1985)].

The discovery of homologous recombination in mammalian cells permits the targeting of new sequences to specific chromosomal loci. Homologous recombination occurs when cultured mammalian cells integrate exogenous DNA into chromosomal DNA at the chromosome location which contains sequences homologous to the plasmid sequences [Folger et al., *Mol. Cell. Biol.* 2:1372–1387 (1982); Folger et al., *Symp. Quant. Biol.* 49:123–138 (1984); Kucherlapati et al., *Proc. Natl. Acad. Sci. USA* 81:3153–3157 (1984); Lin et al., *Proc. Natl. Acad. Sci. USA* 82:1391–1395 (1985); de Saint Vincent et al., *Proc. Natl. Acad. Sci. USA* 80:2002–2006 (1983); Shaul et al., *Proc. Natl. Acad. Sci. USA* 82:3781–3784 (1985)]. The potential for homologous recombination within cells permits the modification of endogenous genes in situ. Conditions have been found where the chromosomal sequence can be modified by introducing into the cell a plasmid DNA which contains a segment of DNA homologous to the target locus and a segment of new sequences with the desired modification [Thomas et al., *Cell* 44:419–428 (1986); Smithies et al., *Nature* 317:230–234 (1985); Smith et al., *Symp. Quant. Biol.* 49:171–181 (1984)]. Homologus recombination between mammalian cell chromosomal DNA and the exogenous plasmid DNA can result in the integration of the plasmid or in the replacement of some of the chromosomal sequences with homologous plasmid sequences. This can result in placing a desired new sequence at the endogenous target locus.

The process of homologous recombination has been evaluated using genes which offer dominant selection such as NEO and HPRT for a few cell types [Song et al., *Proc. Natl. Acad. Sci. USA* 84:6820–6824 (1987); Rubinitz and Subramani, *Mol. Cell Biol.* 6:1608–1614 (1986); and Liskay, *Cell* 35:157–164 (1983)]. Recently, procedures for modifying antibody molecules and for producing chimeric antibody molecules using homologous recombination to target gene modification have been described [Fell et al., *Proc. Natl. Acad. Sci. USA* 86:8507–8511 (1989); and co-pending U.S. patent applications Ser. No. 243,873 filed Sep. 14, 1988, and Ser. No. 468,035 filed Jan. 22, 1990, assigned to the same assignee as the present application, all of which are incorporated by reference herein].

The most direct way to apply antitumor monoclonal antibodies clinically is to administer them in unmodified form, using monoclonal antibodies which display antitumor activity in vitro and in animal models. Most monoclonal antibodies to tumor antigens do not appear to have any antitumor activity by themselves, but certain monoclonal antibodies are known which mediate complement-dependent cytotoxicity (CDC), i.e. kill human tumor cells in the presence of human serum as a source of complement [see, e.g. Hellstrom et al., *Proc. Natl. Acad. Sci. USA* 82:1499–1502 (1985)], or antibody-dependent cellular cytotoxicity (ADCC) together with effector cells such as human NK cells or macrophages. To detect ADCC and CDC activity monoclonal antibodies are tested for lysing cultured $^{51}$Cr-labeled tumor target cells over a 4-hour incubation period.

Target cells are labeled with $^{51}$Cr and then exposed for 4 hours to a combination of effector cells (in the form of human lymphocytes purified by the use of a lymphocyte-separation medium) and antibody, which is added in concentrations varying between 0.1 µg/ml and 10 µg/ml. The release of $^{51}$Cr from the target cells is measured as evidence of tumor-cell lysis (cytotoxicity). Controls include the incubation of target cells alone or with either lymphocytes or monoclonal antibody separately. The total amount of $^{51}$Cr that can be released is measured and ADCC is calculated as the percent killing of target cells observed with monoclonal antibody plus effector cells as compared to target cells being incubated alone. The procedure for CDC is identical to the one used to detect ADCC except that human serum, as a source of complement, (diluted 1:3 to 1:6) is added in place of the effector cells.

Monoclonal antibodies with ADCC and CDC activity are considered for therapeutic use because they often have anti-tumor activities in vivo. Antibodies lacking ADCC and CDC activity in vitro, on the other hand, are commonly ineffective in vivo unless used as carriers of antitumor agents. The ability of a monoclonal antibody to activate the host's complement may prove to be therapeutically beneficial not only because tumor cells may be killed, but also because the blood supply to tumors may increase, thus facilitating the uptake of drugs [see Hellstrom et al., "Immunological Approaches to Tumor Therapy: Monoclonal Antibodies, Tumor Vaccines, and Anti-Idiotypes, in Covalently Modified Antigens and Antibodies in Diagnosis and Therapy, Quash & Rodwell, eds., Marcel Dekker, pp. 15–18 (1989)]. Among mouse monoclonal antibodies, the IgG2a and IgG3 isotypes are most commonly associated with ADCC and CDC. Antibodies having both ADCC and CDC activity have high selectivity for killing only the tumor cells to which they bind and would be unlikely to lead to toxic effects if nonspecifically trapped in lung, liver or other organs. This may give such antibodies an advantage over radiolabelled antibodies or certain types of immunoconjugates.

Very few antibodies are able to kill tumor cells by themselves, that is, in the absence of effector cells or complement as in ADCC or CDC. BR96 is such an antibody, because it can kill cells by itself at an antibody concentration of approximately 10 µg/ml or higher. Such antibodies are of particular interest since they can interfere with some key event in the survival of neoplastic cells.

It is thus apparent that an antibody that displays a high degree of selectivity to a wide range of carcinomas, has anti-tumor activity by itself, and is capable of being readily internalized by tumor cells, may be of great benefit in tumor therapy.

SUMMARY OF THE INVENTION

The present invention provides internalizing antibodies that are highly selective for a range of human carcinomas. More specifically, the novel antibodies of the invention, designated as BR96 antibodies, are a murine monoclonal antibody and a chimeric antibody that bind to a cell membrane antigen found on human carcinoma cells. The antibodies are highly reactive with carcinoma cells, such as those derived from breast, lung, colon and ovarian carcinomas, showing no or limited reactivity with normal human cells or other types of tumors such as lymphomas or sarcomas. In addition, the antibodies of the invention internalize within the carcinoma cells to which they bind and they are capable of killing tumor cells by themselves, i.e., not in conjugated form, and without effector cells or complement. Thus the BR96 antibodies are of particular use in therapeutic applications, for example to react with tumor cells, and in conjugates as a target-selective carrier of various agents which have antitumor effects including chemotherapeutic drugs, toxins, immunological response modifiers, enzymes and radioisotopes. The antibodies can thus be used as a component of various immunoconjugates including antibody-drug and antibody-toxin conjugates where internalization of the conjugate is favored, and after radiolabelling to deliver radioisotope to tumors. The BR96 antibodies can also be therapeutically beneficial even in the unmodified form. Furthermore, the antibodies are useful for in vitro or in vivo diagnostic methods designed to detect carcinomas.

BRIEF DESCRIPTION OF THE DRAWINGS

Figure 3:
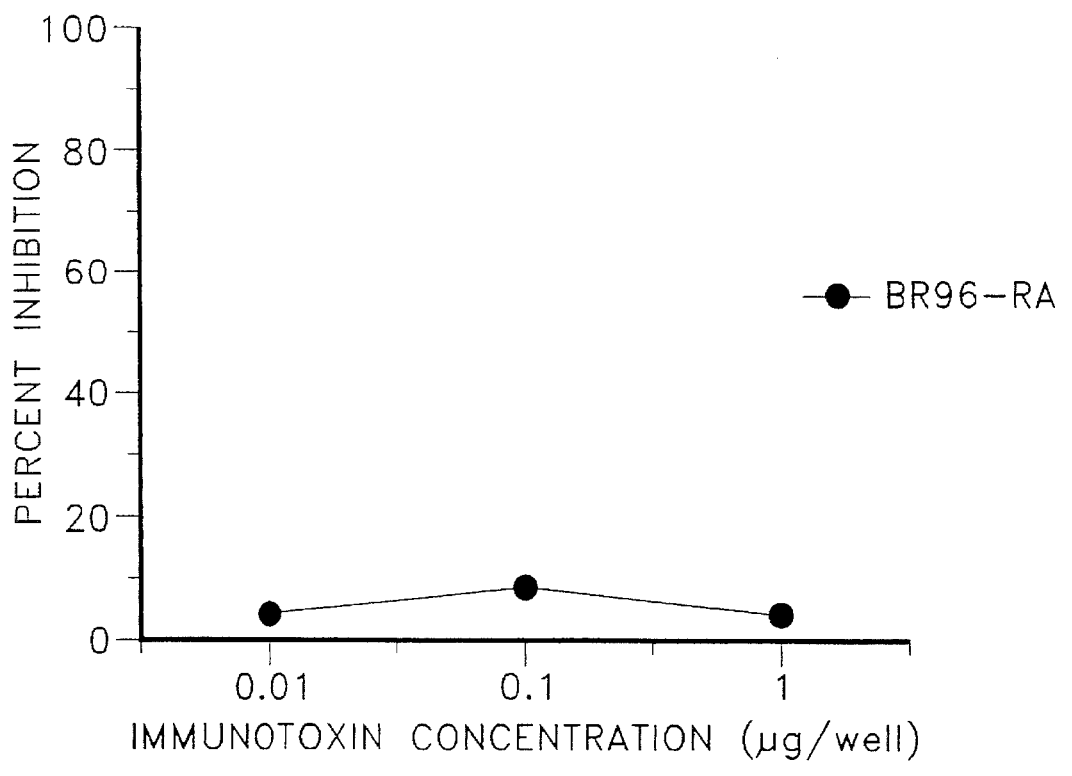

FIG. 3 depicts the percent inhibition of thymidine incorporation into the DNA of HCT116 colon carcinoma cells treated with a BR96-RA immunotoxin at varying concentrations as described in Example 3, infra. BR96 does not bind to HCT 116 cells.

DETAILED DESCRIPTION OF THE INVENTION

Figure 1:
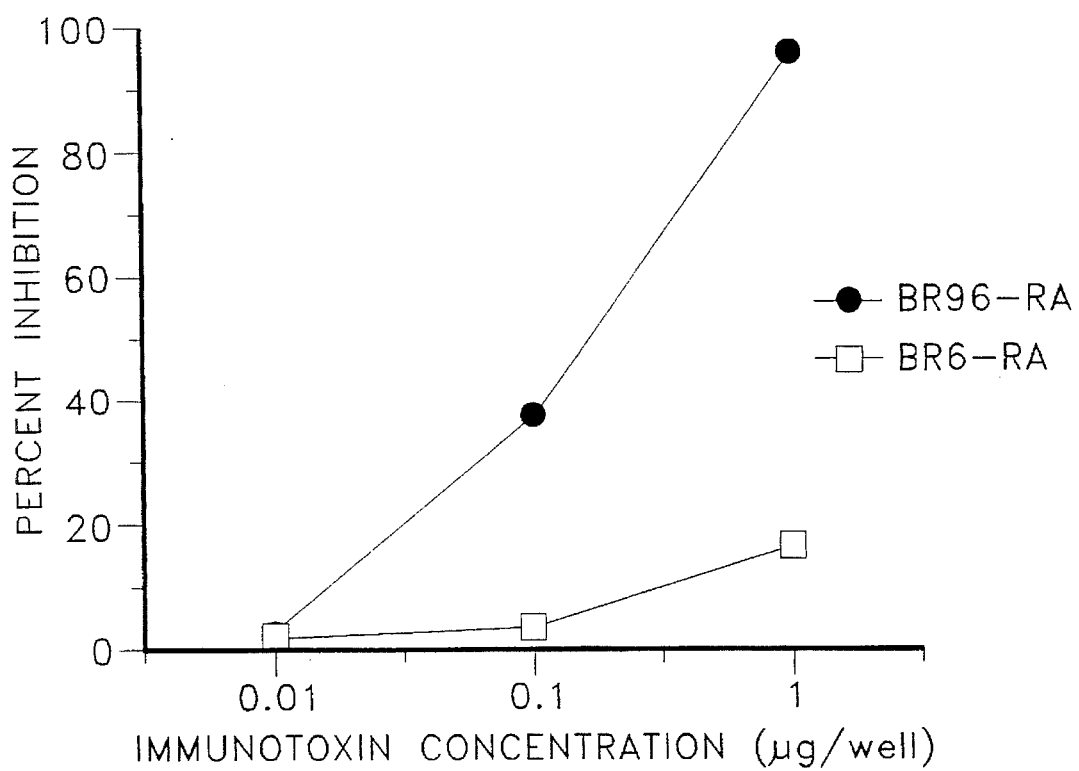
FIG. 1 depicts the percent inhibition of thymidine incorporation into the DNA of 3396 breast carcinoma cells treated with a BR96-RA immunotoxin at varying concentrations as described in Example 3, infra. BR6-RA is an internalizing antibody which is used as a negative control because it does not bind to the 3396 cells.
Figure 2:
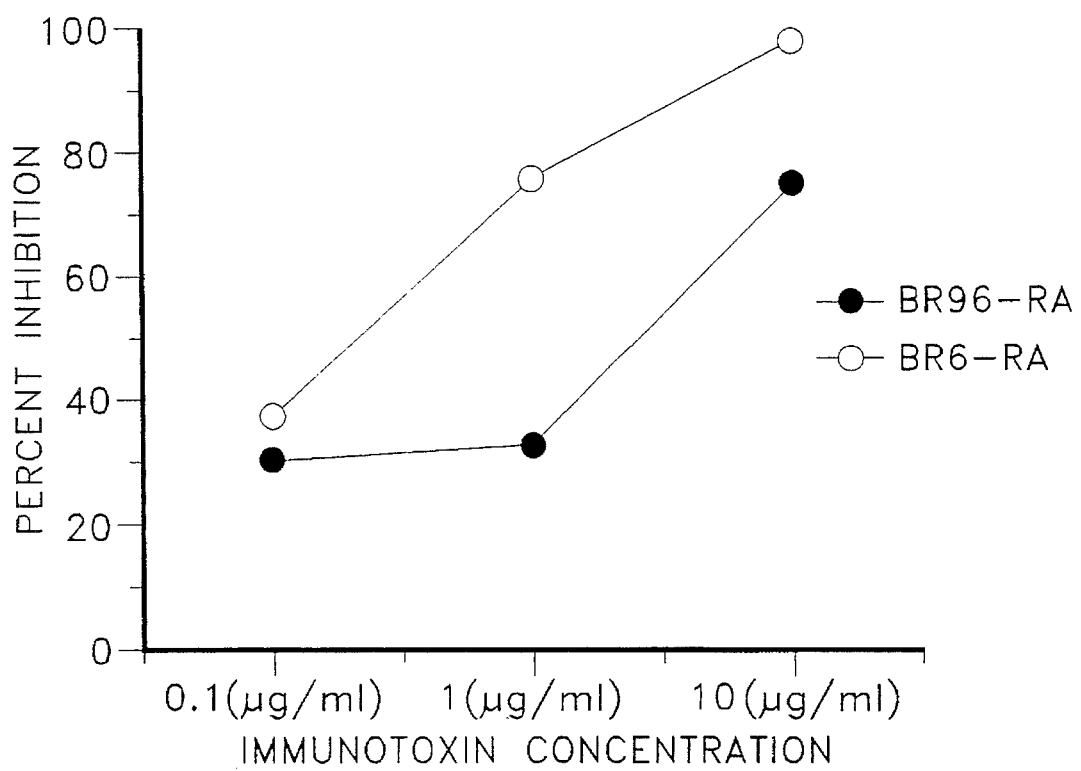
FIG. 2 depicts the percent inhibition of thymidine incorporation into the DNA of 2707 lung carcinoma cells treated with a BR96-RA immunotoxin at varying concentrations as described in Example 3, infra. BR6-RA is an internalizing antibody which also binds to the 2707 cells.
Figure 4:
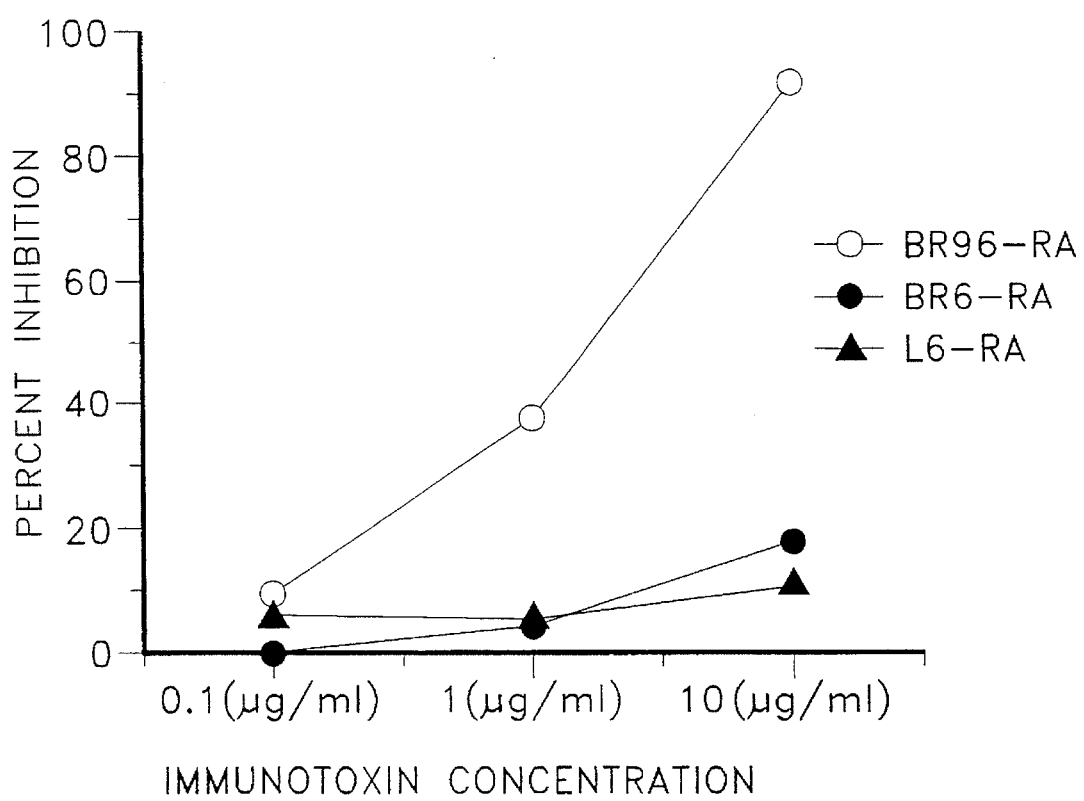
FIG. 4 depicts the percent inhibition of thymidine incorporation into the DNA of C colon carcinoma cells treated with a BR96-RA immunotoxin at varying concentrations as described in Example 3, infra. BR6-RA does not bind to the C cells; L6-RA binds to the C cells but does not internalize.

In order that the invention herein described may be more fully understood, the following detailed description is set forth.

The present invention relates to novel antibodies that are highly specific for carcinoma cells. More particularly, the antibodies react with a range of carcinomas such as breast, lung, ovary and colon carcinomas, while showing none or limited reactivity with normal human tissues or other types of tumors such as sarcomas or lymphomas.

The BR96 antibodies can be used to isolate and characterize the antigen to which they bind. Thus, the BR96 antibodies can be used as a probe to identify and characterize the epitope recognized and to further define the cell membrane antigen with which they react [see, e.g., Nudelman et al., "Characterization of Human Melanoma-Associated Ganglioside Antigen Defined By A Monoclonal Antibody, 4.2", *J. Biol. Chem.*, 257 (1)12752–56 (1982) and Hakomori, "Tumor Associated Carbohydrate Antigens", *Ann Rev. Immunol*, 2:103–26 (1984)].

Results of preliminary epitope screens conducted on monoclonal antibody BR96 have indicated that the antigen on the carcinoma cells to which BR96 antibody binds is a fucosylated variant of the Lewis Y antigen. The Lewis Y (Le$^y$) antigen has been described by Abe et al., *J. Biol. Chem.* 258:8934 (1983); Lloyd et al., *Immunogenetics* 17:537 (1983); Brown et al., *Biosci. Rep*,. 3:163 (1983); Hellstrom et al., *Cancer Res.* 46:3917 (1986). Fucosylated Lewis Y antigen has been described by Abe et al., *Cancer Res.* 46:2639–2644 (1986).

The monoclonal antibody of the invention can be produced using well-established hybridoma techniques first introduced by Kohler and Milstein [see, Kohler and Milstein, "Continuous Cultures Of Fused Cells Secreting Antibody Of Pre-Defined Specificity", *Nature*, 256:495–97 (1975). See, also, Brown et al., "Structural Characterization Of Human Melanoma-Associated Antigen p97 with Monoclonal Antibodies", *J. Immunol.*, 127 (2):539–46 (1981)]; Brown et al., "Protein Antigens Of Normal And Malignant Human Cells Identified By Immunoprecipitation With Monoclonal Antibodies", *J. Biol. Chem.*, 255:4980–83 (1980); Yeh et al., "Cell Surface Antigens Of Human Melanoma Identified By Monoclonal Antibody", *Proc. Natl. Acad. Sci. USA*, 76(6):297–31 (1979); and Yeh et al., "A Cell-Surface Antigen Which is Present In the Ganglioside Fraction And Shared By Human Melanomas", *Int. J. Cancer*, 29:269–75 (1982).]

These techniques involve the injection of an immunogen (e.g., cells or cellular extracts carrying the antigen or purified antigen) into an animal (e.g., a mouse) so as to elicit a desired immune response (i.e., antibodies) in that animal. After a sufficient time, antibody-producing lymphocytes are obtained from the animal either from the spleen, lymph nodes or peripheral blood. Preferably, the lymphocytes are obtained from the spleen. The splenic lymphocytes are then fused with a myeloma cell line, usually in the presence of a fusing agent such as polyethylene glycol (PEG). Any of a number of myeloma cell lines may be used as a fusion partner according to standard techniques; for example, the P3-NS1/1A$_g$4-1, P3-x63-Ag8.653 or Sp2/O Ag14 myeloma lines. These myeloma lines are available from the American Type Culture Collection, ("ATCC") in Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting conditions to obtain isolated clones. The supernatants of the hybridomas are screened for the presence of antibody of that desired specificity, e.g., by immunoassay techniques using the antigen that had been used for immunization. Positive clones can then be subcloned under limiting dilution conditions and the monoclonal antibody produced can be isolated. Hybridomas produced according to these methods can be propagated in vitro or in vivo (in ascites fluid) using techniques known in the art [see, generally, Fink et al., supra at page 123, FIGS. 6–11]. Commonly used methods for purifying monoclonal antibodies include ammonium sulfate precipitation, ion exchange chromatography, and affinity chromatography [see, e.g., Zola et al., "Techniques For The Production And Characterization Of Monoclonal Hybridoma Antibodies", in *Monoclonal Hybridoma Antibodies: Techniques And Applications*, Hurell (ed.), pp. 51–52 (CRC Press 1982)].

According to a preferred embodiment, a monoclonal antibody of this invention, designated BR96, was produced via the hybridoma techniques described hereinbelow using a breast cancer cell line 3396 as the immunogen. The BR96 hybridoma, prepared as described hereinbelow and producing the BR96 antibody, was deposited on Feb. 22, 1989 with the American Type Culture Collection (ATCC), 12301 Parklawn Drive, Rockville, Md. 20852, and has there been identified as follows:

BR96 ATCC Accession No.: HB 10036

The BR96 antibody is of the IgG3 subclass. The antibody displays a high specificity for carcinoma cells of different organ types, for example, tumors of the breast, lung, colon and ovary as well as cultured cell lines established from various breast, lung and colon carcinomas. Furthermore, the BR96 antibody shows no binding to other types of tumor cells such as the T-cell lymphoma cells lines, CEM and MOLT-4, the B cell lymphoma cell line P3HR-1 or melanoma cells lines. The BR96 antibody is able to be internalized in antigen-positive tumor cells, is toxic on antigen-positive tumor cells, mediates ADCC and CDC activity, and surprisingly, is cytotoxic alone, i.e. in unmodified form. The BR96 antibodies appear to recognize a Le$^y$ antigen.

According to another embodiment, F(ab')$_2$ fragments of the BR96 monoclonal antibody were produced by pepsin digestion of purified BR96 Lamoyi et al., "Preparation of F(ab')$_2$ Fragments from Mouse IgG of various Subclasses", *Meth. Enzymol.* 121:652–663 (1986)], as described hereinbelow. The binding of the F(ab')$_2$ fragments to tumor (3396) and MCF7 cells was shown to be comparable to the binding of the whole BR96 monoclonal antibody.

In another preferred embodiment, the chimeric (murine/human) antibody of the invention was produced using a two-step homologous recombination procedure as described by Fell et al., in *Proc. Natl. Acad. Sci. USA* 86:8507–8511 (1989) and in patent application U.S. Ser. No. 243,873, filed Sep. 14, 1988, (now U.S. Pat. No. 5,204,244), and Ser. No. 468,035, filed Jun. 22, 1990, (now U.S. Pat. No. 5,202,238), assigned to the same assignee as the present application; the disclosures of all of these documents are incorporated in their entirety by reference herein. This two-step protocol involves use of a target vector encoding human IgGgamma1 heavy chain to transfect a mouse hybridoma cell line expressing murine BR96 monoclonal antibody (hybridoma ATCC No. HB 10036) to produce a hybridoma expressing a BR96 chimeric antibody containing human IgGgamma1 heavy chain. This hybridoma is then transfected with a target vector containing DNA encoding human kappa (K) light chain to produce a murine hybridoma expressing a BR96 chimeric antibody containing human IgGgamma1 heavy chain and human K light chain. The target vectors used to transfect the hybridomas are the pHgamma1HC-DD$_4$ vector digested with Xba1 enzyme (Oncogen, Seattle, Wash.) and the HindIII digested pSV$_2$gpt/C$_K$ vector (Oncogen, Seattle, Wash.).

The chimeric BR96 hybridoma, identified herein as ChiBR96, prepared as described hereinbelow and producing the chimeric human/murine BR96 antibody, was deposited on May 23, 1990, with the American Type Culture Collection (ATCC), 12301 Parklawn Drive, Rockville, Md. 20852, and has there been identified as follows:

ChiBR96 ATCC Accession No.: HB 10460

Once the hybridoma that expresses the chimeric antibody is identified, the hybridoma is cultured and the desired chimeric molecules are isolated from the cell culture supernatant using techniques well known in the art for isolating monoclonal antibodies.

The term "BR96 antibody" as used herein includes whole, intact polyclonal and monoclonal antibody materials such as the murine BR96 monoclonal antibody produced by hybridoma ATCC No. HB 10036, and chimeric antibody molecules such as chimeric BR96 antibody produced by hybridoma ATCC No. 10460. The BR96 antibody described above includes any fragments thereof containing the active antigen-binding region of the antibody such as Fab, F(ab')$_2$ and Fv fragments,using techniques well established in the art [see, e.g., Rouseaux et al., "Optimal Conditions For The Preparation of Proteolytic Fragments From Monoclonal IgG of Different Rat IgG Subclasses", in *Methods Enzymol.*, 121:663–69 (Academic Press 1986)]. The BR96 antibody of the invention also includes fusion proteins.

In addition, the BR96 antibody of this invention does not display any immunohistologically detectable binding to normal human tissues from major organs, such as kidney, spleen, liver, skin, lung, breast, colon, brain, thyroid, heart, lymph nodes or ovary. Nor does the antibody react with peripheral blood leukocytes. BR96 antibody displays limited binding to some cells in the tonsils and testes, and binds to acinar cells in the pancreas, and to epithelial cells in the stomach and esophagus. Thus, the BR96 antibody is superior to most known antitumor antibodies in the high degree of specificity for tumor cells as compared to normal cells [see, e g., Hellstrom et al., "Immunological Approaches To Tumor Therapy: Monoclonal Antibodies, Tumor Vaccines, And Anti-Idiotypes", in *Covalently Modified Antigens And Antibodies In Diagnosis And Therapy*, Quash/Rodwell (eds.), pp. 1–39 (Marcell Dekker, Inc., 1989) and Bagshawe, "Tumour Markers—Where Do We Go From Here", *Br. J. Cancer*, 48:167–75 (1983)].

In addition, the present invention encompasses antibodies that are capable of binding to the same antigenic determinant as the BR96 antibodies and competing with the antibodies for binding at that site. These include antibodies having the same antigenic specificity as the BR96 antibodies but differing in species origin, isotype, binding affinity or biological functions (e.g., cytotoxicity). For example, class, isotype and other variants of the antibodies of the invention having the antigen-binding region of the BR96 antibody can be constructed using recombinant class-switching and fusion techniques known in the art [see, e.g., Thammana et al., "Immunoglobulin Heavy Chain Class Switch From IgM to IgG In A Hybridoma", *Eur. J. Immunol.*, 13:614 (1983); Spira et al., "The Identification Of Monoclonal Class Switch Variants By Subselection And ELISA Assay", *J. Immunol. Meth.*, 74:307–15 (1984); Neuberger et al., "Recombinant Antibodies Possessing Novel Effector Functions", *Nature* 312: 604–608 (1984); and Oi et al., "Chimeric Antibodies", *Biotechniques*, 4 (3):214–21 (1986)]. Thus, other chimeric antibodies or other recombinant antibodies (e.g., fusion proteins wherein the antibody is combined with a second protein such as a lymphokine or a tumor inhibitory growth factor) having the same binding specificity as the BR96 antibodies fall within the scope of this invention.

Also included within the scope of the invention are anti-idiotypic antibodies to the BR96 antibody of the invention. These anti-idiotypic antibodies can be produced using the BR96 antibody and the fragments thereof as immunogen and are useful for diagnostic purposes in detecting humoral response to tumors and in therapeutic applications, e.g., in a vaccine, to induce an anti-tumor response in patients [see, e.g., Nepom et al., "Anti-Idiotypic Antibodies And The Induction Of Specific Tumor Immunity", in *Cancer And Metastasis Reviews*, 6:487–501 (1987)].

The BR96 antibody of the invention is also useful for diagnostic applications, both in vitro and in vivo, for the detection of human carcinomas that possess the antigen for which the antibodies are specific. In vitro diagnostic methods include immunohistological detection of tumor cells (e.g., on human tissue, cells or excised tumor specimens) or serologic detection of tumor-associated antigens (e.g., in blood samples or other biological fluids).

Immunohistochemical techniques involve staining a biological specimen such as a tissue specimen with the BR96 antibody of the invention and then detecting the presence on the specimen of the antibody complexed to its antigen. The formation of such antibody-antigen complexes with the specimen indicates the presence of carcinoma cells in the tissue. Detection of the antibody on the specimen can be accomplished using techniques known in the art such as immunoenzymatic techniques, e.g., the immunoperoxidase staining technique or the avidin-biotin (ABC) technique, or immunofluorescence techniques [see, e.g., Ciocca et al., "Immunohistochemical Techniques Using Monoclonal Antibodies", *Meth. Enzymol.*, 121:562–79 (1986); Hellstrom et al., "Monoclonal Mouse Antibodies Raised Against Human Lung Carcinoma", *Cancer Research*, 46:3917–23 (1986); and Kimball (ed.), *Introduction To Immunology* (2nd Ed.), pp. 113–117 (Macmillan Pub. Co. 1986)]. For example, immunoperoxidase staining was used as described in Example 2, infra, to demonstrate the reactivity of the BR96 antibody with lung, breast, colon, and ovary carcinomas and the low reactivity of the antibody with normal human tissue specimens.

Serologic diagnostic techniques involve the detection and quantitation of tumor-associated antigens that have been secreted or "shed" into the serum or other biological fluids of patients thought to be suffering from carcinoma. Such antigens can be detected in the body fluids using techniques known in the art such as radioimmunoassays (RIA) or enzyme-linked immunosorbent assays (ELISA) wherein an antibody reactive with the "shed" antigen is used to detect the presence of the antigen in a fluid sample [see, e.g., Uotila et al., "Two-Site Sandwich ELISA With Monoclonal Antibodies To Human AFP", *J. Immunol. Methods*, 42:11 (1981) and Allum et al., supra at pp. 48–51]. These assays, using the BR96 antibodies disclosed herein, can therefore be used for the detection in biological fluids of the glycolipid antigen with which the BR96 antibodies react and thus the detection of human carcinoma in patients. Thus, it is apparent from the foregoing that the BR96 antibodies of the invention can be used in most assays involving antigen-antibody reactions. These assays include, but are not limited to, standard RIA techniques, both liquid and solid phase, as well as ELISA assays, immunofluorescence techniques, and other immunocytochemical assays [see, e.g., Sikora et al. (eds), *Monoclonal Antibodies*, pp. 32–52 (Blackwell Scientific Publications 1984)].

The invention also encompasses diagnostic kits for carrying out the assays described above. In one embodiment, the diagnostic kit comprises the BR96 monoclonal antibody, fragments thereof, fusion proteins or chimeric antibody of the invention, and a conjugate comprising a specific binding partner for the BR96 antibody and a label capable of producing a detectable signal. The reagents can also include ancillary agents such as buffering agents and protein stabilizing agents (e.g., polysaccharides). The diagnostic kit can further comprise, where necessary, other components of the signal-producing system including agents for reducing background interference, control reagents or an apparatus or container for conducting the test. In another embodiment, the diagnostic kit comprises a conjugate of the BR96 antibodies of the invention and a label capable of producing a detectable signal. Ancillary agents as mentioned above can also be present.

The BR96 antibody of the invention is also useful for in vivo diagnostic applications for the detection of human carcinomas. One such approach involves the detection of tumors in vivo by tumor imaging techniques. According to this approach, the BR96 antibody is labeled with an appropriate imaging reagent that produces a detectable signal. Examples of imaging reagents that can be used include, but are not limited to, radiolabels such as $^{131}$I, $^{111}$In, $^{123}$I, $^{99m}$Tc, $^{32}$P, $^{125}$I, $^3$H, and $^{14}$C, fluorescent labels such as fluorescein and rhodamine, and chemiluminescers such as luciferin. The antibody can be labeled with such reagents using techniques known in the art. For example, see Wensel and Meares, *Radioimmunoimaging And Radioimmunotherapy*, Esevier, New York (1983) for techniques relating to the radiolabeling of antibodies [see also, Colcher et al., "Use Of Monoclonal Antibodies As Radiopharmaceuticals For The Localization Of Human Carcinoma Xenografts In Athymic Mice", *Meth Enzymol.*, 121:802–16 (1986)].

In the case of radiolabeled antibody, the antibody is administered to the patient, localizes to the tumor bearing the antigen with which the antibody reacts, and is detected or "imaged" in vivo using known techniques such as radionuclear scanning using, e.g., a gamma camera or emission tomography [see, e.g., Bradwell et al., "Developments In Antibody Imaging", in *Monoclonal Antibodies For Cancer Detection And Therapy*, Baldwin et al. (eds.), pp. 65–85 (Academic Press 1985)]. The antibody is administered to the patient in a pharmaceutically acceptable carrier such as water, saline, Ringer's solution, Hank's solution or nonaqueous carriers such as fixed oils. The carrier may also contain substances that enhance isotonicity and chemical stability of the antibody such as buffers or preservatives. The antibody formulation is administered, for example, intravenously, at a dosage sufficient to provide enough gamma emission to allow visualization of the tumor target site. Sufficient time should be allowed between administration of the antibody and detection to allow for localization to the tumor target. For a general discussion of tumor imaging, see Allum et al., supra at pp. 51–55.

The properties of the BR96 antibody: a) very high specificity for tumor cells; b) internalization; c) toxicity to antigen-positive tumor cells alone, i.e. in unmodified form, when used at appropriate concentrations; and d) CDC and ADCC activity, suggest a number of in vivo therapeutic applications. First, the BR96 antibody can be used alone to target and kill tumor cells in vivo. The antibody can also be used in conjunction with an appropriate therapeutic agent to treat human carcinoma. For example, the antibody can be used in combination with standard or conventional treatment methods such as chemotherapy, radiation therapy or can be conjugated or linked to a therapeutic drug, or toxin, as well as to a lymphokine or a tumor-inhibitory growth factor, for delivery of the therapeutic agent to the site of the carcinoma. Techniques for conjugating such therapeutic agents to antibodies are well known [see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243–56 (Alan R. Liss, Inc. 1985); Hellstrom et al., "Antibodies For Drug Delivery", in *Controlled Drug Delivery* (2nd Ed.), Robinson et al. (eds.), pp. 623–53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475–506 (1985); and Thorpe et al., "The Preparation And Cytotoxic Properties Of Antibody-Toxin Conjugates", *Immunol. Rev.*, 62:119–58 (1982)]. The BR96 antibody of the invention is particularly suited for use in a therapeutic conjugate because it is readily internalized within the carcinoma cells to which it binds and thus can deliver the therapeutic agent to intracellular sites of action.

Alternatively, the BR96 antibody can be coupled to high-energy radiation, e.g., a radioisotope such as $^{131}I$, which, when localized at the tumor site, results in a killing of several cell diameters [see, e.g., Order, "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303–16 (Academic Press 1985)]. According to yet another embodiment, the BR96 antibody can be conjugated to a second antibody to form an antibody heteroconjugate for the treatment of tumor cells as described by Segal in U.S. Pat. No. 4,676,980.

Still other therapeutic applications for the BR96 antibody of the invention include conjugation or linkage, e.g., by recombinant DNA techniques, to an enzyme capable of converting a prodrug into a cytotoxic drug and the use of that antibody-enzyme conjugate in combination with the prodrug to convert the prodrug to a cytotoxic agent at the tumor site [see, e.g., Senter et al., "Anti-Tumor Effects Of Antibody-alkaline Phosphatase", *Proc Natl. Acad. Sci. USA*, 85:4842–46 (1988); "Enhancement of the in vitro and in vivo Antitumor Activities of Phosphorylated Mitomycin C and Etoposide Derivatives by Monoclonal Antibody-Alkaline Phosphatase Conjugates", *Cancer Research* 49:5789–5792 (1989); and Senter, "Activation of Prodrugs by Antibody-Enzyme Conjugates: A New Approach to Cancer Therapy, FASEB J. 4:188–193 (1990)]. Still another therapeutic use for the BR96 antibody involves use, either in the presence of complement or as part of an antibody-drug or antibody-toxin conjugate, to remove tumor cells from the bone marrow of cancer patients. According to this approach, autologous bone marrow may be purged ex vivo by treatment with the antibody and the marrow infused back into the patient [see, e.g., Ramsay et al., "Bone Marrow Purging Using Monoclonal Antibodies", *J. Clin. Immunol.*, 8(2):81–88 (1988)].

Furthermore, chimeric or other recombinant BR96 antibodies of the invention, as described earlier, may be used therapeutically. For example, a fusion protein comprising at least the antigen-binding region of the BR96 antibody joined to at least a functionally active portion of a second protein having anti-tumor activity, e.g., a lymphokine or oncostatin, may be used to treat human carcinoma in vivo. Furthermore, recombinant techniques known in the art can be used to construct bispecific antibodies wherein one of the binding specificities of the antibody is that of BR96 [see, e.g. U.S. Pat. No. 4,474,893].

Finally, anti-idiotypic antibodies of the BR96 antibody may be used therapeutically in active tumor immunization and tumor therapy [see, e.g., Hellstrom et al., "Immunological Approaches To Tumor Therapy: Monoclonal Antibodies, Tumor Vaccines, And Anti-Idiotypes", in *Covalently Modified Antigens And Antibodies In Diagnosis And Therapy*, supra at pp. 35–41].

It is apparent therefore that the present invention encompasses pharmaceutical compositions, combinations and methods for treating human carcinomas. For example, the invention includes pharmaceutical compositions for use in the treatment of human carcinomas comprising a pharmaceutically effective amount of a BR96 antibody and a pharmaceutically acceptable carrier. The compositions may contain the BR96 antibody either unmodified, conjugated to a therapeutic agent (e.g., drug, toxin, enzyme or second antibody) or in a recombinant form (e.g., chimeric or bispecific BR96). The compositions may additionally include other antibodies or conjugates for treating carcinomas (e.g., an antibody cocktail).

The antibody compositions of the invention can be administered using conventional modes of administration including, but not limited to, intravenous, intraperitoneal, oral, intralymphatic or administration directly into the tumor. Intravenous administration is preferred.

The antibody compositions of the invention may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The antibody compositions also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment and the judgment of the treating physician. Accordingly, the dosages of the compositions should be titrated to the individual patient. Nevertheless, an effective dose of the, antibody compositions of this invention may be in the range of from about 1 to about 2000 mg/m².

In order that the invention described herein may be more fully understood, the following examples are set forth. It should be understood that these examples are for illustrative purposes only and are not to be construed as limiting the scope of this invention in any manner.

EXAMPLE 1

Preparation Of The BR96 Monoclonal Antibody

The BR96 monoclonal antibody of the invention was produced using hybridoma fusion techniques as described previously by M. Yeh et al., *Proc. Natl. Acad. Sci. USA*, (1979), Supra and Yeh et al., *Int. J. Cancer* (1982), supra. Briefly, a three month-old BALB/c mouse was immunized using as the immunogen explanted cultured cells from a human breast adenocarcinoma, designated 3396 or H3396 (from adenocarcinoma of the breast from a patient which had been established in culture at Oncogen, Seattle, Wash.). The mouse received injections on five occasions: on the first four occasions, the mouse received one intraperitoneal injection and 1 subcutaneous injection split between 4 sites on the mouse. On the fifth occasion, the mouse was given only one intraperitoneal injection. The total number of cells injected on each occasion was approximately $10^7$ cells. Three days after the last immunization, the spleen was removed and spleen cells were suspended in RPMI culture medium. The spleen cells were then fused with P3-x63-Ag8.653 mouse myeloma cells in the presence of polyethylene glycol (PEG) and the cell suspension grown in microtiter wells in selective HAT medium as described by Yeh et al., supra [see, also, Kohler and Milstein, *Nature*, 256:495–97 (1975) and *Eur. J. Immunol.*, 6:511–19 (1976)]. The mixture was seeded to form low density cultures originating from single fused cells or clones.

The supernatants from these hybridoma cultures were then screened for direct binding activity on the breast cancer cell line, 3396, and a fibroblast cell line obtained from a skin biopsy using an ELISA assay similar to that described by Douillard et al., "Enzyme-Linked Immunosorbent Assay For Screening Monoclonal Antibody Production Using Enzyme-Labeled Second Antibody", *Meth. Enzymol.*, 92:168–74 (1983).

According to this assay, the antigen (with which the antibody being screened for is reactive) is immobilized on microtiter plates and then incubated with hybridoma supernatants. If a supernatant contains the desired antibody, the antibody will bind to the immobilized antigen and is detected by addition of an anti-immunoglobulin antibody-enzyme conjugate and a substrate for the enzyme which leads to a measurable change in optical density. In the present studies, breast cancer cells or control fibroblast cells were dispensed into a 96-well tissue culture plate (Costar Cambridge, Mass.) and incubated overnight in a humid 37° C. incubator (5% $CO_2$). The cells were then fixed with 100 µl of freshly prepared 1.0% glutaraldehyde to a final well concentration of 0.5% and incubated 15 min at room temperature, followed by washing three times with 1×phosphate buffered saline (PBS). The cells were next blocked for 30 min with 5% bovine serum albumin (BSA) in PBS and washed again three times with PBS. The supernatants from the hybridoma cultures were then added at 100 µl/well, the wells incubated for 1 h at room temperature, and the cells washed three times with PBS. Next, goat anti-mouse horseradish peroxidase (Zymed, Calif.) diluted in 0.1% BSA and PBS was added to a concentration of 100 µl/well. The reaction mixture was incubated for either 1 h at room temperature or 30 min at 37° C. and the cells were then washed three times with PBS. o-Phenylenediamine (OPD) was then added at 100 µl/well and the plates incubated in the dark at room temperature for 5–45 min. Antibody binding to the cells was detected by a color change in the wells that occurred within 10–20 min. The reaction was stopped by adding 100 µl/well $H_2SO_4$ and the absorbance read in a Dynatech (Alexandria, Va.) Microelisa autoreader at 490 nm.

It should be noted that this assay can be performed using intact cells or purified soluble antigen or cellular extracts as the immobilized antigen. When soluble antigen or cell extracts were used as antigen, the antigen was initially plated at 50 µl/well in PBS and the plates were incubated overnight at room temperature before beginning the assay. When using intact cells as antigen, they may be used fresh or after fixation. In either case, the cells were initially plated at $10^4$ cells in 100 µl/well in culture medium and incubated overnight in a 37° C. incubator (5% $CO_2$).

Hybridomas which produced antibodies binding to the breast cancer cell line and not to the human fibroblast cells were thus selected, and tested in a FACS cell sorter on peripheral blood leukocytes (PBLs), as described in Example 2, infra. Hybridomas that were negative on PBLs were cloned, expanded in vitro, and further tested for antibody specificity. Those hybridomas producing antibody reactive with human breast cancer were recloned, expanded, and injected into pristane-primed 3-month old BALB/c mice, where they grew as ascites tumors.

Following this procedure, hybridoma cell line BR96 was obtained, cloned and injected into mice to develop as an ascites tumor. As disclosed above, the BR96 hybridoma has been deposited with the ATCC. Monoclonal BR96 antibody was purified from ascites by affinity chromatography on immobilized recombinant protein A (Repligen, Cambridge, Mass.). Clarified ascites was diluted with an equal volume of binding buffer (1M potassium phosphate, pH 8) and applied to a protein A column previously equilibrated with binding buffer. The column was extensively washed with binding buffer and then the antibody was eluted with 50 mM phosphoric acid, pH 3. The purified antibody fraction was neutralized with 1M Tris, pH 9 and then dialyzed against phosphate buffered saline. Purified BR96 was finally sterile filtered and stored refrigerated or frozen.

EXAMPLE 2

Characterization Of The BR96 Monoclonal Antibody

Isotype Determination

To determine the class of immunoglobulin produced by the BR96 hybridoma, the following techniques were utilized:
(a) Ouchterlony Immunodiffusion An aliquot of supernatant of the hybridoma cells was placed into the center well of the a 25% agar plate. Monospecific rabbit anti-mouse Ig isotype antibodies (Southern Biotechnology, Birmingham, Ala.) were placed in the outer wells and the plate was incubated for 24–28 h at room temperature. Precipitation lines were then read.
(b) ELISA Isotyping Dynatech Immulon 96-well plates were coated with goat anti-mouse Ig antibodies at 1 µg/ml concentration, 50 µl/well in PBS and left covered overnight at 4° C. The plates were washed with PBS/Tween 20, 0.05% and blocked with medium at 100 μl/well for 1 h at room temperature. After washing the plates, supernatants from the BR96 hybridoma were added and incubated at room temperature for 1 h. After washing with PBS containing 2% bovine serum albumin (BSA), plates were incubated at 37° C. for 30 min with monospecific rabbit anti-mouse Ig isotype antibodies coupled to peroxidase (Zymed, South San Francisco, Calif.). After further washing, the plates were incubated with 1 mg/ml OPD and 0.03% $H_2O_2$ in 0.1M citrate buffer, pH 4.5. Optical density at 630 nm was determined on a Dynatec ELISA plate reader.

Based on these procedures, it was determined that the BR96 monoclonal antibody is of the IgG3 isotype.

Characteristics Of The BR96 Monoclonal Antibody

The BR96 antibody shows a high degree of reactivity with a wide range of carcinomas and displays only limited reactivity with normal cells. This was shown by experiments involving immunohistological studies on frozen tissue sections as well as binding studies using intact cultured cells.

Immunohistology

The peroxidase-antiperoxidase (PAP) technique of L. A. Sternberger as described in *Immunochemistry*, pp. 104–69 (John Wiley & Sons, New York, 1979) and as modified by H. J. Garrigues et al., "Detection Of A Human Melanoma-Associated Antigen, p97, In Histological Sections Of Primary Human Melanomas", *Int. J. Cancer*, 29:511–15 (1982), was used for the immunohistological studies. The target tissues for these tests were obtained at surgery and frozen within 4 h of removal using isopentane precooled in liquid nitrogen. Tissues were then stored in liquid nitrogen or at −70° C. until used. Frozen sections were prepared, air dried, treated with acetone and dried again [see Garrigues et al., supra]. Sections to be used for histologic evaluation were stained with hematoxylin. To decrease non-specific backgrounds sections were preincubated with normal human serum diluted ⅕ in PBS [see Garrigues et al., Supra]. Mouse antibodies, rabbit anti-mouse IgG, and mouse PAP were diluted in a solution of 10% normal human serum and 3% rabbit serum. Rabbit anti-mouse IgG (Sternberger-Meyer Immunochemicals, Inc., Jarettsville, Md.), was used at a dilution of ¹⁄₅₀. Mouse PAP complexes (Sternberger-Meyer Immunochemicals, Inc.) containing 2 mg/ml of specifically purified PAP was used at a dilution of ¹⁄₈₀.

The staining procedure consisted of treating serial sections with either specific antibody, i.e., BR96, or a control antibody for 2.5 h, incubating the sections for 30 min at room temperature with rabbit anti-mouse IgG diluted ¹⁄₅₀ and then exposing the sections to mouse PAP complexes diluted ¹⁄₈₀ for 30 min at room temperature. After each treatment with antibody, the slides were washed twice in PBS.

The immunohistochemical reaction was developed by adding freshly prepared 0.5% 3,3'-diaminobenzidine tetrahydrochloride (Sigma Chemical Co., St. Louis, Mo.) and 0.01% $H_2O_2$ in 0.05M Tris buffer, pH 7.6, for 8 min [see Hellstrom et al., *J. Immunol.*, 127:157–60 (1981)]. Further exposure to a 1% $OsO_4$ solution in distilled water for 20 min intensified the stain. The sections were rinsed with water, dehydrated in alcohol, cleared in xylene, and mounted on slides. Parallel sections were stained with hematoxylin.

The slides were each evaluated under code and coded samples were checked by an independent investigator. Typical slides were photographed by using differential interference contrast optics (Zeiss-Nomarski). The degree of antibody staining was evaluated as 0 (no reactivity), + (a few weakly positive cells), ++ (at least one third of the cells positive), +++ (most cells positive), ++++ (approximately all cells strongly positive). Because differences between + and 0 staining were less clear cut than between + and ++ staining, a staining graded as ++ or greater was considered "positive". Both neoplastic and stroma cells were observed in tumor samples. The staining recorded is that of the tumor cells because the stroma cells were not stained at all or were stained much more weakly than the tumor cells.

Table 1 below demonstrates the immunohistological staining of various tumor and normal tissue specimens using the BR96 monoclonal antibody. As the table clearly demonstrates, the BR96 antibody reacts with a wide range of human carcinoma specimens, does not react with sarcoma and displays only infrequent reactivity with melanoma. Furthermore, it shows only limited reactivity with any of the large number of normal human tissues tested. The only reactivity detected with normal cells detected was binding to a small subpopulation of cells in the tonsils and in the testis, and to acinar cells in the pancreas, and to epithelial cells of the stomach and esophagus.

TABLE 1

Immunoperoxidase Staining of Human Tumors and Normal Tissue Specimens with BR96 Monoclonal Antibody

| TISSUE TYPE | NUMBER POSITIVE/ NUMBER TESTED | |
|---|---|---|
| Tumors | | |
| Lung carcinoma (non-small cell) | 14/17 | |
| Breast carcinoma | 17/19 | |
| Colon carcinoma | 15/18 | |
| Ovary carcinoma | 4/4 | |
| Endometrial carcinoma | 2/2 | |
| Melanoma | 2/5 | |
| Sarcoma | 0/5 | |
| Stomach carcinoma | 2/2 | |
| Pancreatic carcinoma | 2/2 | |
| Esophagus carcinoma | 2/2 | |
| Cervical carcinoma | 2/2 | |
| Normal Tissues | | |
| Lung | 0/7 | |
| Spleen | 0/5 | |
| Breast | 0/2 | |
| Colon | 0/7 | |
| Kidney | 0/7 | |
| Liver | 0/5 | |
| Brain | 0/2 | |
| Heart | 0/3 | |
| Skin | 0/2 | |
| Thyroid | 0/2 | |
| Adrenal | 0/1 | |
| Ovary | 0/2 | |
| Lymph nodes | 0/2 | |
| Lymphocyte pellet | 0/4 | |
| Pancreas | 2/2 | (only acinar cells were positive) |
| Uterus | 0/7 | |
| Retina | 0/1 | |
| Testis | 2/2 | (only small subpopulation of cells were positive) |
| Tonsil | 2/2 | (only small subpopulation of cells were positive) |
| Stomach | 2/2 | (epithelial cells positive) |
| Esophagus | 2/2 | (epithelial cells positive) |

The binding of the BR96 antibody to various cultured cell lines was also evaluated. Antibody binding to the cell surface of intact cultured cells was identified either by a direct binding assay with $^{125}$I-labeled antibody as described in Brown et al., "Quantitative Analysis Of Melanoma-Associated Antigen p97 In Normal And Neoplastic Tissues", *Proc Natl. Acad. Sci. USA*, 78:539–43 (1981), or by direct immunofluorescence using a Coulter Epics C fluorescence activated cell sorter (FACS) II [Hellstrom et al., *Cancer Res.* 46:3917–3923 (1986)].

For binding analyses using a FACS cell sorter, $2 \times 10^5$ to $1 \times 10^6$ cultured cells were aliquoted in 15% fetal bovine serum (FBS) in IMDM media (Gibco, New York) to a total volume of 500 µl/tube. The cells were centrifuged for 1.5 min on a Serofuge and the supernatant removed. 100 µl of the BR96 monoclonal antibody at 10 µl/ml was added to each tube, the contents of which was then mixed and incubated on ice for 30 min. The reaction mixture was washed three times with 500 µl of 15% FBS/IMDM by centrifugation for 1.5 min on the Serofuge (tubes were blotted after the third wash). Then, 50 µl of optimized FITC-conjugated goat anti-mouse IgG antibody (Tago, Burlingame, Calif.) diluted 1:25 in 15% FBS/IMDM was added to each tube and the reaction mixture was mixed and incubated for 30 min. The wash step was then repeated and after blotting of the tubes, each pellet was resuspended in 200–500 µl of PBS. Each sample was run on a Coulter Epics C FACS and the mean fluorescence intensity (MFI) was determined. From the MFI, the linear fluorescent equivalent (LFE) was determined. The LFE of each test sample divided by the LFE of a negative control gave a ratio between the brightness of cells stained by specific versus control antibody. The binding data is shown in Table 2 below.

TABLE 2

FACS Analysis of the Binding of BR96 to Various Types of Suspended Cells

| Cell line | Ratio (10 µg/ml) |
|---|---|
| Breast carcinoma 3396 | 54 |
| Breast carcinoma MCF-7 | 38 |
| Breast carcinoma 3630 | 22 |
| Breast carcinoma 3680 | 22 |
| Lung carcinoma 2987 | 15 |
| Lung carcinoma 2707 | 30 |
| Lung carcinoma 2964 | 2 |
| Lung carcinoma 3655-3 | 18 |
| Colon carcinoma RCA | 34 |
| Colon carcinoma 3619 | 22 |
| Colon carcinoma 3347 | 5 |
| Colon carcinoma HCT116 | 1 |
| Colon carcinoma CB5 | 27 |
| Colon carcinoma C | 30 |
| Colon carcinoma 3600 | 16 |
| Ovary carcinoma 3633-3 | 11 |
| Melanoma 2669 | 1 |
| Melanoma 3606 | 1 |
| Melanoma 3620 | 1 |
| T cell lymphoma line CEM | 1 |
| T cell lymphoma line MOLT-4 | 1 |
| B cell lymphoma line P3HR1 | 1 |
| Peripheral blood leukocytes | 1 |

As Table 2 demonstrates, the BR96 monoclonal antibody reacted with breast, lung and colon carcinoma cell lines but did not react with melanoma lines or with T or B lymphoma lines nor with normal peripheral blood leukocytes. Scatchard analysis using radiolabeled antibody indicated that the approximate association constant ($K_a$) of BR96 was calculated to be $3.6 \times 10^6$ antigen sites/cell for the 3396 line which binds BR96.

These data demonstrate that monoclonal antibody BR96 recognize cell surface antigens abundantly expressed (up to $10^6$ molecules/cell) on the majority of human carcinomas.

EXAMPLE 3

Internalization Of The BR96 Monoclonal Antibody Within Carcinoma Cells

Studies were conducted to measure internalization of the BR96 monoclonal antibody within antigen-positive carcinoma cells. According to one procedure, BR96 was conjugated to the ricin A chain toxin to form an immunotoxin, BR96-RA, whose internalization by carcinoma cells was then determined. Uptake of the conjugate by the carcinoma cells was assessed by determining to what extent the tumor cells were killed by ricin A chain.

Conjugation of the antibody to the toxin was carried out as follows: Deglycosylated ricin-A chain (Inland Labs, Austin, Tex.) [see, also, Blakey et al., *Cancer Res.*, 47:947–952 (1987)] was treated with dithiothreitol (5 mM) prior to gel filtration on G-25 Sephadex using PBS, pH 7.2 as eluant. This was added in a 2:1 molar ratio to the antibody in PBS, the antibody having been previously modified with N-succinimidyl-3-(2-pyridyldithio)propionate (SPDP) (Pierce, Rockford, Ill.) according to the procedure of Lambert et al., *J. Biol. Chem.*, 260:12035–12041 (1985). Reaction was allowed to proceed for 12–24 h at room temperature, and the solution was then diluted with 1 volume of $H_2O$. Removal of unconjugated antibody was achieved using Blue Sepharose CL-6B (Pharmacia, Uppsala, Sweden) [see Knowles et al., *Anal. Biochem.*, 160:440–443 (1987)].

The conjugate and excess ricin-A chain were eluted with high salt (10×PBS) and subjected to further purification on Sephacryl-300 (Pharmacia) using PBS as eluant. The resulting conjugate was free of unbound monoclonal antibody or ricin A-chain and consisted mostly of 1:1 adducts.

The internalization of BR96-RA by various carcinoma cell lines was then measured using a thymidine uptake inhibition assay. According to this assay, the inhibition of $^3$H-thymidine incorporation into the DNA of the carcinoma cells (i.e., the inhibition of cell proliferation) is a measure of the cytotoxic effect of BR96-RA on the cells and thus a measure of the internalization of the immunotoxin within the cell.

For the assay, carcinoma cells were plated into a 96-well microtiter plate at $1 \times 10^4$ cells/well in 100 µl of IMDM medium with 15% fetal calf serum (FCS). The plates were incubated for 12–18 h at 37° C. to let the cells adhere. Then the media was removed. Plates were kept on ice. The BR96-RA immunotoxin (100 µl) was then added in log 10 serial dilutions, starting at 10 µg/ml final concentration down to 0.01 µg/ml. The reaction mixture was incubated for 4 h on ice. The plates were washed and 200 µl/ml media was added and further incubated at 37° C. for 18 h. At this point, 50 µl of $^3$H-thymidine was added at 1 µCi/well and the plates incubated for 6 h at 37° C. in a 5% $CO_2$ incubator. The assay plates were then frozen at −70° C. for at least 1 h and thawed in a gel dryer for 15 min. The cells were harvested onto glass fiber filters (Filter Strips, No. 240-1, Cambridge Technology) in plastic scintillation vials using a PHD cell harvester. 3 ml of scintillation counting liquid was added to the vials and the vials were counted on a Beckman LS3891 beta scintillation counter at 1 minute per sample.

Graphs of the percent inhibition of thymidine incorporation vs. immunotoxin concentration for each cell line tested were plotted and are shown in FIGS. 1–5. In each assay, a control was run. The results of the assay are expressed as a percentage of the $^3$H thymidine incorporated by untreated control cells.

Figure 5:
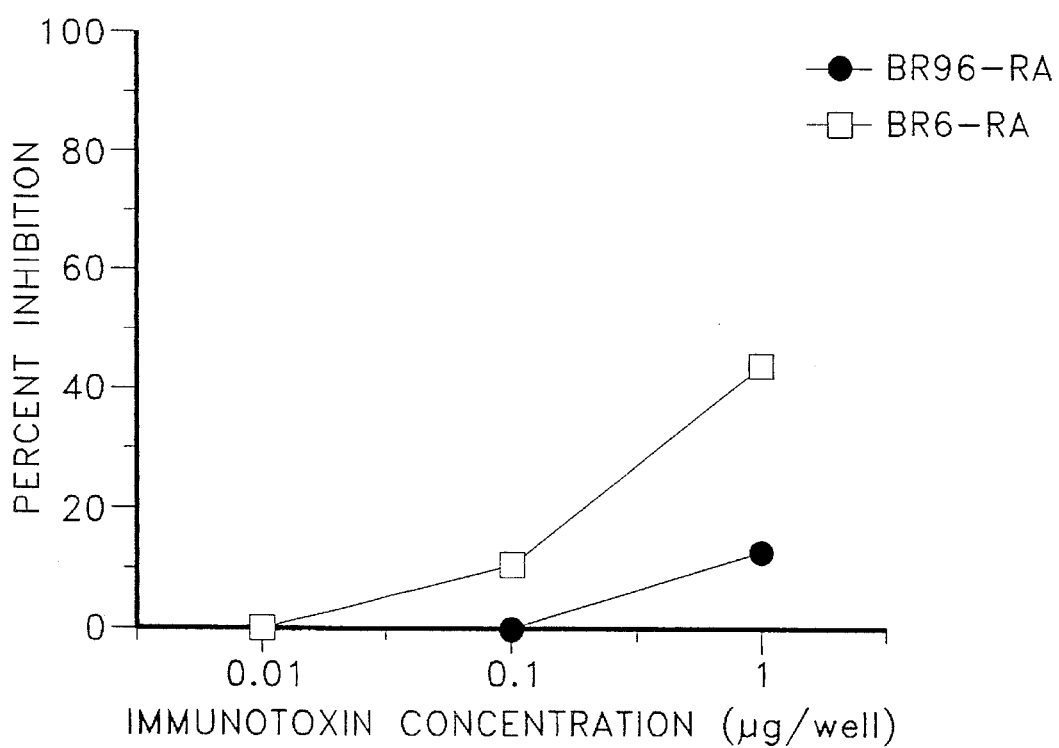
FIG. 5 depicts the percent inhibition of thymidine incorporation into the DNA of 3347 colon carcinoma cells treated with a BR96-RA immunotoxin at varying concentrations as described in Example 3, infra. BR96 does not bind to these cells while BR6 does.

FIG. 1 depicts the percent inhibition of thymidine incorporation by cells from the 3396 breast carcinoma cell line caused by internalization of BR96-RA. Similar results were obtained with the 2707 lung carcinoma cell line (FIG. 2) and C colon carcinoma cell line (see FIG. 4). The BR96-RA was not internalized by HCT 116 cell line, a human colon carcinoma cell line that does not bind BR96 (see FIG. 3). FIG. 5 shows no internalization of BR96-RA on 3347, a colon carcinoma cell line to which BR96 does not bind; BR6RA, on the other hand, which binds to the 3347 cells, does internalize. This study, therefore, demonstrated not only internalization of the BR96 antibody but the selectivity of the internalization of the BR96 antibody for antigen positive carcinoma cells.

EXAMPLE 4

Cytotoxicity of Unmodified BR96 Monoclonal Antibody

Three types of experiments were performed to follow up on the unexpected observation that monoclonal antibody BR96 appeared to be cytotoxic by itself (i.e., in unmodified state) when tested in a FACS assay. So as to avoid an effect of complement in serum, all sera used were heat inactivated (56° C. for 30 min); in addition, some of the experiments with FACS analysis (as described below) were performed on cells which were grown in serum-free medium and tested in the absence of serum.

Figure 6:
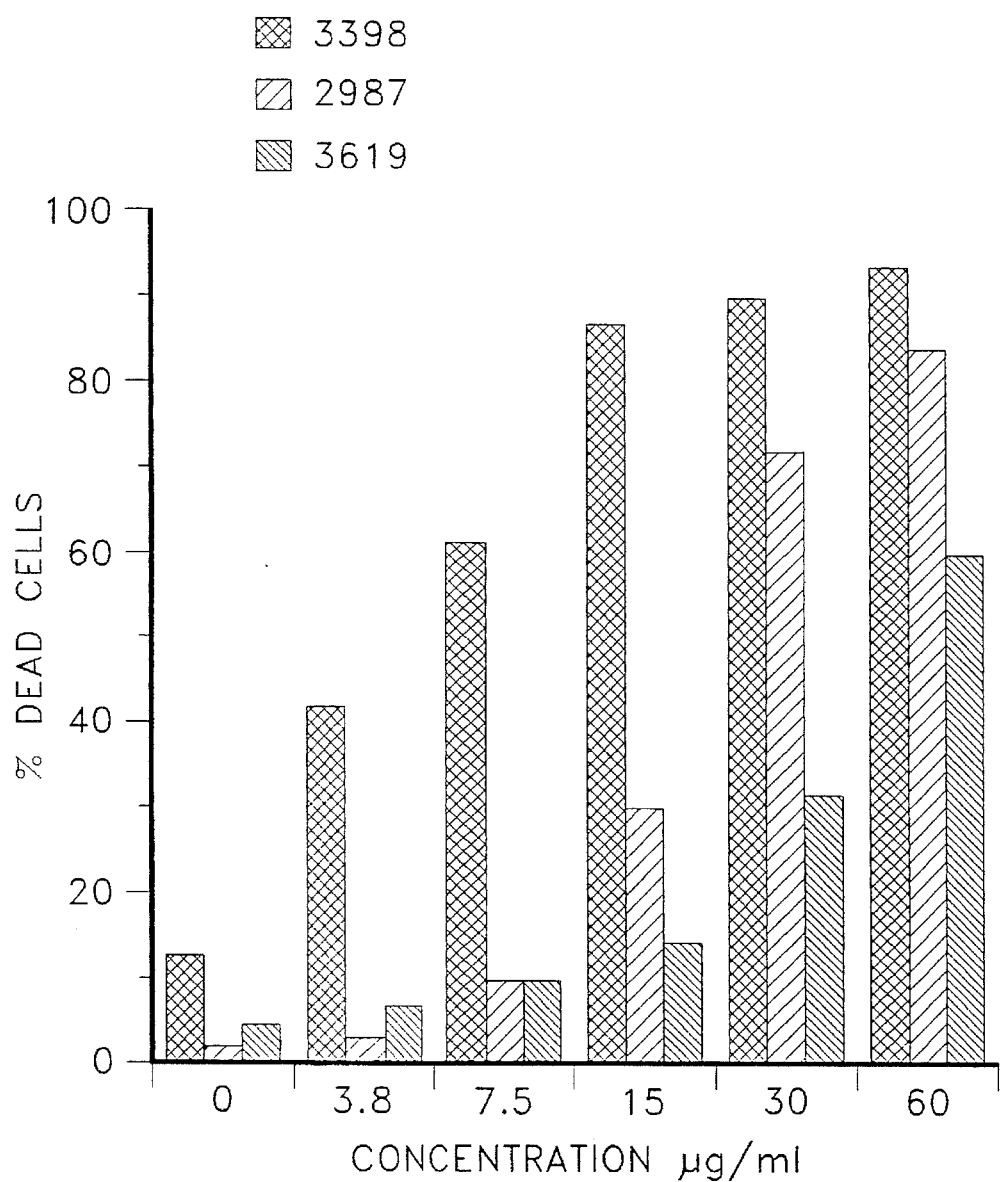
FIG. 6 depicts the results of FACS analysis of the cytotoxicity of propidium iodide stained 3396 breast carcinoma cells, 2987 lung carcinoma cells and 3619 colon carcinoma cells, as described in Example 4, infra.

First, living suspended cells from a variety of antigen positive carcinoma lines (3396, 2987, 3619) were treated with monoclonal antibody BR96. Cells ($5 \times 10^5$) were incubated on ice for 30 min with 100 µl of BR96 or control monoclonal antibody at a concentration of 60, 30, 15, 7.5 and 3.8 µg/ml in culture medium (IMDM, 15% FBS). After washing the cells twice with culture medium, the cells were suspended in 500 µl medium and stained by adding the dye propidium iodide which stains dead cells [Krishan, *Cell Biol.* 66:188 (1975); and Yeh, *J. Immunol. Methods*, 43:269 (1981)]. Out of a 1 mg/ml stock solution (in 70% alcohol) 5 µl dye was added to cell samples, incubated on ice for 15 min, washed once and finally suspended in 500 µl medium. The cells were evaluated on a Coulter Epics C FACS, with dead cells being identified by their red fluorescence. The analysis was done on a two-parameter display with log forward lightscatter in the horizontal and log red fluorescence in the vertical display. Computations of cell size versus cell viability were obtained by applying the Coulter Epics C Quadstat program. Tumor cells which could bind BR96 as well as tumor cells not binding BR96 were studied in parallel. The results are shown in FIG. 6. FIG. 6 demonstrates that incubation of cells from any of three antigen-positive carcinomas with BR96 rapidly killed them. Untreated or antigen-negative cells were not killed.

Figure 7:
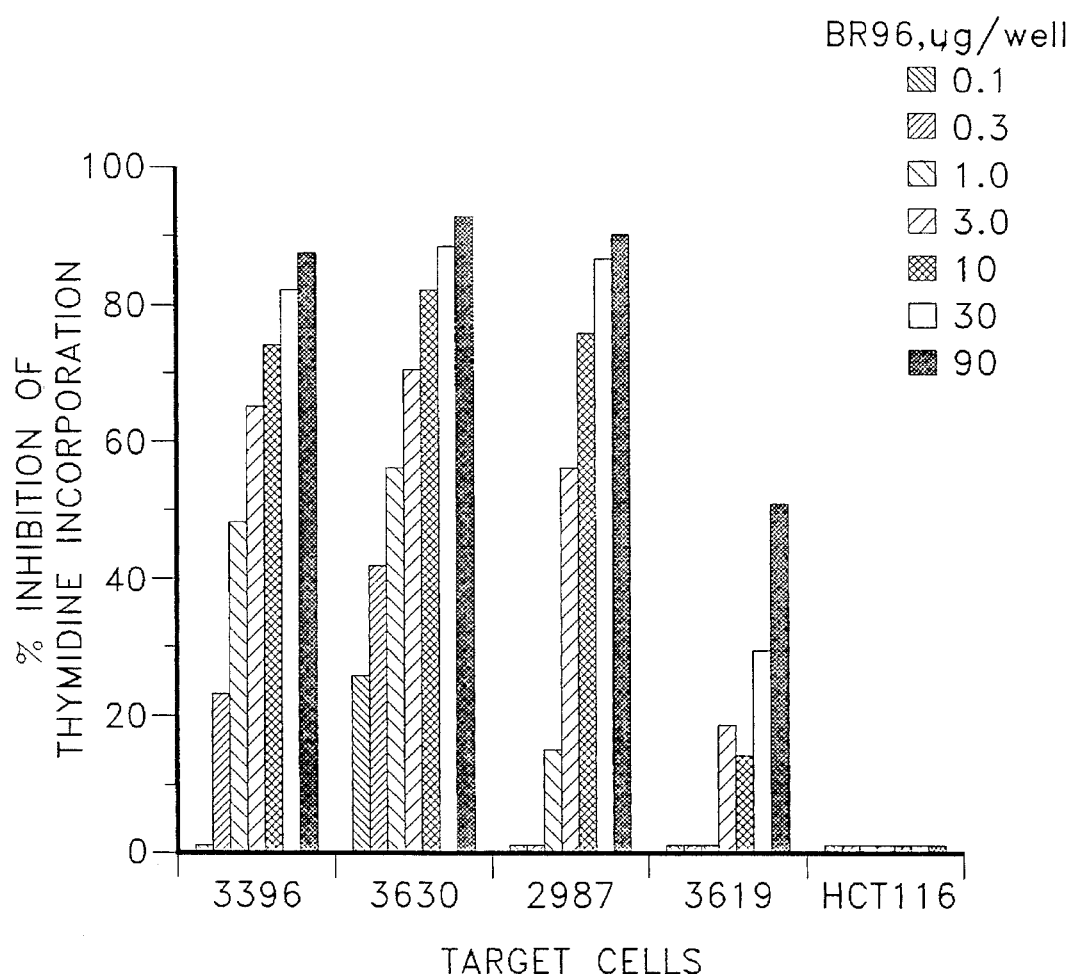
FIG. 7 depicts the effects of BR96 on cell proliferation of various cell lines as described in Example 4, infra.

Second, tumor cells (3396, 3630, 2987, 3619 and HCT 116) were exposed to BR96 (or the control monoclonal antibody) for 18 h at 37° C. in a 96-well microtiter plate at $3 \times 10^3$ cells/well in 150 µl of IMDM medium containing FBS for 66 h after which 50 µl of $^3$H-thymidine was added at 1 µCi/well and the plate was incubated for another 6 h at 37° C. Subsequently, it was frozen at −70° C. for at least 1 h and thawed in a gel dryer for 15 min, and the cells harvested onto glass fiber filters. The tritiated thymidine assay was then performed as described in the preceding example, except that the cells and antibodies were incubated at 37° C. FIG. 7 illustrates the results. BR96 caused an inhibition of [$^3$H]thymidine incorporation into antigen-positive cell lines, and this effect was dose dependent. The antigen-negative cell line HCT116 was not affected by an concentration of BR96.

Figure 8:
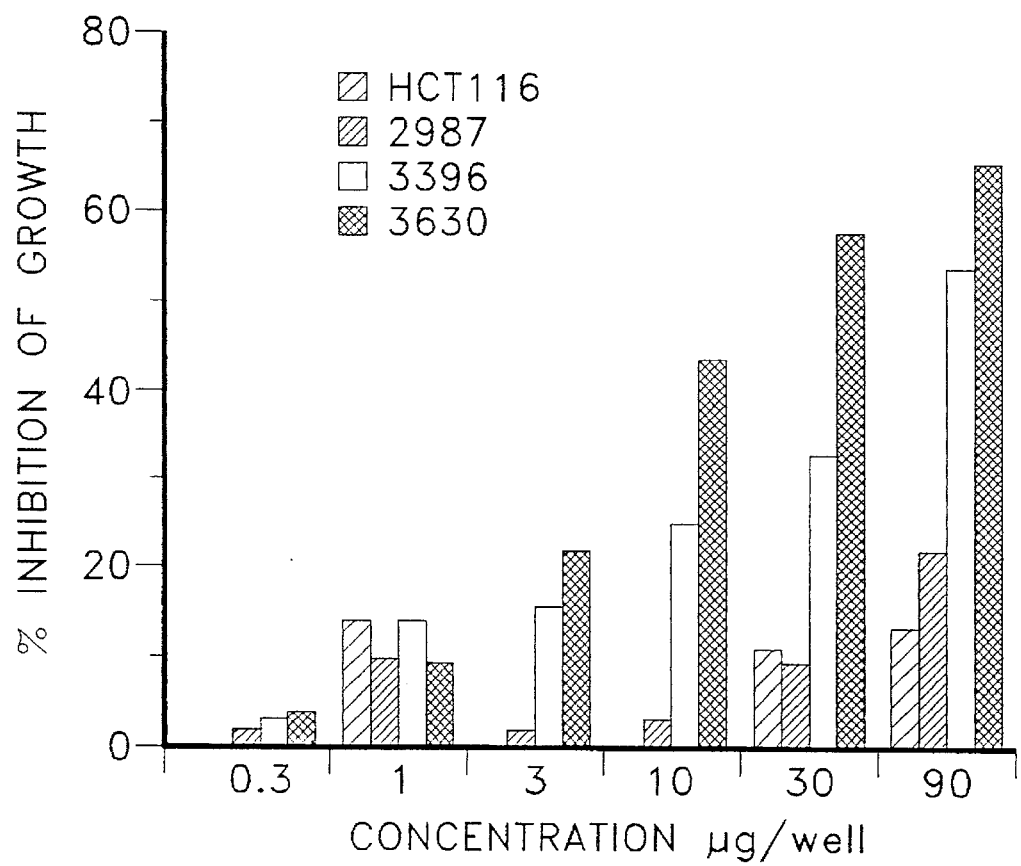
FIG. 8 illustrates the effect of BR96 on cell growth of various cell lines, measured by a staining method as described in Example 4, infra.

Third, using a modification of a procedure described by Linsley et al. [Linsley, et al., "Identification and characterization of cellular receptors for growth regulator, Oncostatin M", *J. Biol. Chem.* 264:4282–4289 (1989)] a growth inhibition assay was performed. Cells from four different cell lines (HCT116, 2987, 3396 and 3630) were seeded ($3 \times 10^3$) in a volume of 0.1 ml of IMDM with 15% fetal bovine serum (FBS) in 96-well microtiter plates and allowed to attach for 3 h at 37° C. Various concentrations of whole BR96 monoclonal were then added in a volume of 0.1 ml, after which incubation at 37° C. was continued for 72 h. Subsequently, the culture medium was removed and the cells were stained by crystal violet (0.1% in 20% methanol) for 30 min. and washed three times with PBS. The bound dye was eluted by the addition of 0.1 ml of a solution of 0.1M sodium citrate, Ph 4.2, in 50% ethanol. Samples were assayed in triplicate on an ELISA reader measuring the absorbance in the presence of BR96 with the absorbance in untreated samples. The results of this procedure are expressed as percentage inhibition of cell growth. FIG. 8 illustrates the results. The results of this assay were in agreement with those presented above for the thymidine incorporation assay (FIG. 7).

EXAMPLE 5

ADCC Activity of BR96 Antibody

Determination of ADCC activity of BR96 monoclonal antibody was performed as described by Hellstrom et al., *Proc. Natl. Acad. Sci. (USA)* 82:1499–1502 (1985). Briefly, a short-term $^{51}$Cr-release test that measures the release of $^{51}$Cr as described by Cerrotini et al., *Adv. Immunol.* 18:67–132 (1974) was used as evidence of tumor-cell lysis (cytotoxicity). Peripheral blood lymphocytes from healthy human subjects were separated on Ficoll-Hypaque [Hellstrom et al., *Int. J. Cancer* 27:281–285 (1981)] to provide effector cells equal to 5% natural killer cell reactivity against SK-MEL-28 cells; ($10^6$) cells were labeled by incubation with 100 µCi (1 Ci=37 Gbq) of $^{51}$Cr for 2 h at 37° C., after which they were washed three times and resuspended in medium. The labeled cells were seeded ($2 \times 10^4$ cells per well in 20 µl) into Microtiter V-bottom plates (Dynatech Laboratories, Alexandria, Va.). Purified antibody BR96 (10 µg/ml, 1 µg/ml, and 0.1 µg/ml) was then added, followed by $2 \times 10^5$ lymphocytes per well in 100 µl. The mixtures were incubated for 2 to 4 h after which the plates were centrifuged at 400×g. The supernatants were removed and the radioactivity in 100 µl samples was measured with a gamma-counter. There were two replicates per group; the variation between replicates was less than 10%. Several "criss-cross" experiments were done, in which lung (or colon) carcinoma and melanoma targets were tested in parallel with monoclonal antibody BR96 and with the antimelanoma monoclonal antibody MG-22 [Hellstrom et al., *Proc. Natl. Acad. Sci. USA*, 82:1499–1502 (1985)] which do not bind to most carcinoma cells. Controls included the incubation of target cells alone or with either lymphocytes or monoclonal antibody separately.

Spontaneous release was defined as the counts per minute (cpm) released into the medium from target cells exposed to neither antibodies nor lymphocytes, and total release, as the number of counts released from target cells that were osmotically lysed at the end of the assay. Percent cytotoxicity was calculated as:

$$\frac{\text{experimental group release} - \text{spontaneous release}}{\text{total release} - \text{spontaneous release}} \times 100$$

Effector cells were characterized by assessing their sensitivity to incubation with anti-serum to the Leu-11b surface marker and guinea pig complement, using procedures described by Hellstrom et al., in *Monoclonal Antibodies and Cancer Therapy*, UCLA Symposia on Molecular and Cellular Biology, New Series, eds. Reisfeld & Sell, Liss, New York, Vol 27, pp. 149–164 (1985), incorporated herein by reference. This was done to measure the expression of the Leu-11b marker, which characterizes natural killer (NK) cells and is expressed by lymphocytes mediating ADCC against human melanoma cells in the presence of monoclonal antibody BR96. The cytotoxicity by effector cells alone ("natural killer effect") was subtracted from the data provided in FIG. 9.

Figure 9:
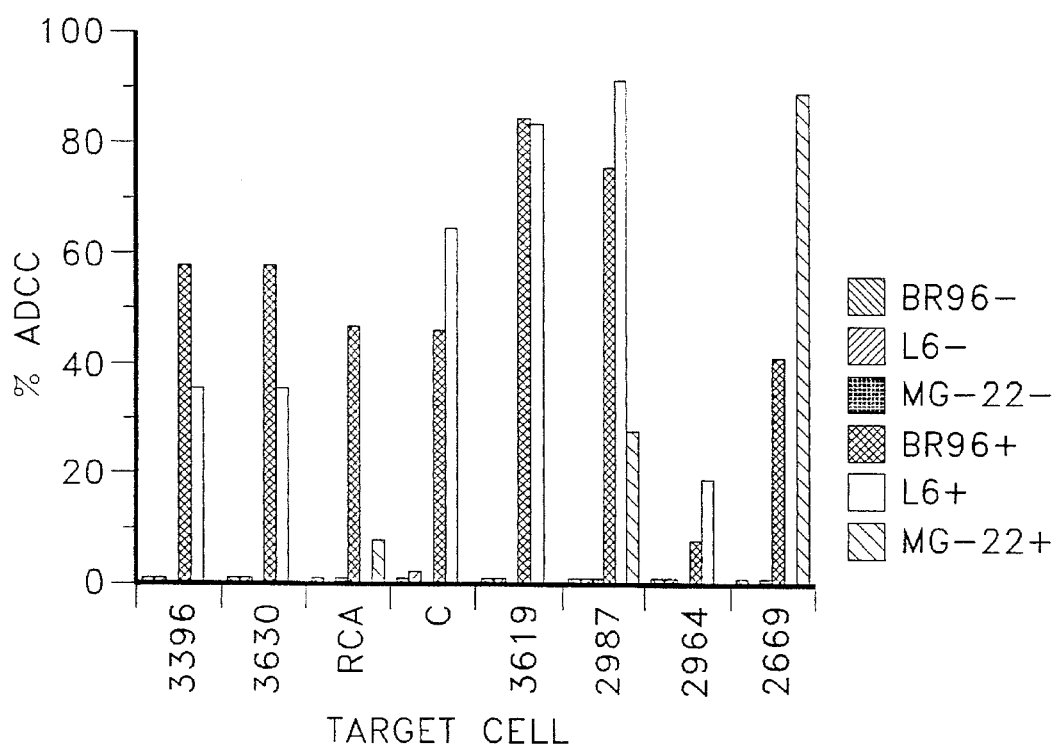
FIG. 9 illustrates the results of tests to determine ADCC activity of BR96 as described in Example 5, infra.

The results shown in FIG. 9 for an antibody concentration of 10 μg/ml indicate that BR96 mediates ADCC activity if present in sufficient concentrations and if the target cells express sufficient concentrations of the epitope. The ADCC activity can be seen at antibody concentrations lower than those at which the antibody is cytotoxic by itself (usually around 20 μg/ml). When antibody BR96 was used alone as a control it produced 0% killing at the concentrations tested and using the $^{51}$Cr assay. ADCC activity was only found with BR96 antibody-binding cell lines. Thus, cells from five different carcinoma lines, which all bound BR96, were killed via ADCC at monoclonal antibody concentrations down to 0.1 μg/ml, while cells from a sixth line, 2964, which did not bind BR96, were not killed. The requirement for antibody binding to obtain ADCC was further demonstrated by the fact that both of the two carcinomas which could bind a different antibody, L6 (lines 3619 and 2987), were killed by L6 via ADCC, while the others were not. Under the conditions of the assay, BR96 alone caused the release of only 1% of the label, even when tested at a concentration of 10 μg/ml.

EXAMPLE 6

Ability of BR96 to Mediate Complement-Mediated Cytotoxicity. (CDC)

Tests to evaluate the ability of monoclonal antibody BR96 to kill tumor cells in the presence of human serum as a source of complement (complement-mediated cytotoxicity) (CDC) were performed similarly to those for the ADCC tests described in Example 5, supra, except that 100 μl of human serum from normal human subjects as the source of complement diluted 1:3 to 1:6 was added per microtest well in place of a suspension of effector cells.

Figure 10:
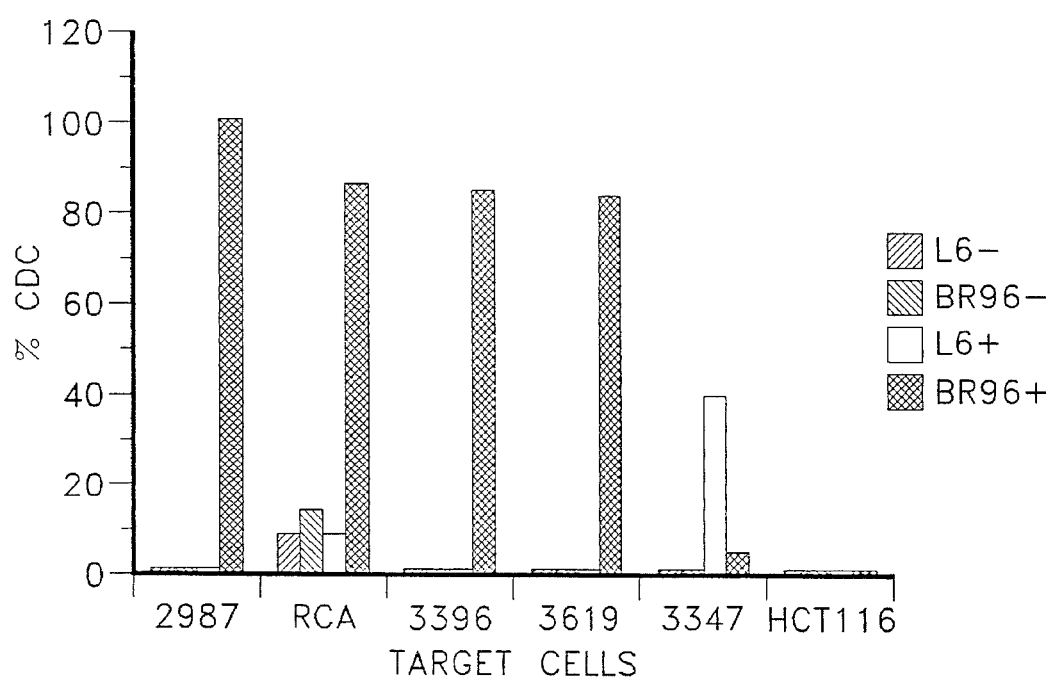
FIG. 10 describes the results of tests to determine CDC activity of BR96 as described in Example 6, infra.

As shown in FIG. 10, CDC against cells binding BR96 was seen at an antibody concentration Of 0.1–5.0 μg/ml, while there was no CDC against the BR96 antigen-negative lines HCT116 and 3347. The 3347 cells could, however, be killed when using the L6 monoclonal antibody, which binds to these cells. Controls were always included in which BR96 was tested in the absence of complement. No killing by BR96 alone was detected by the $^{51}$Cr release assay. These data show that BR96 gave a cytotoxic effect in the presence of human serum at concentrations where it is not cytotoxic by itself. (Control antibody gave no CDC).

EXAMPLE 7

Determination of Reactivity of BR96 to Glycolipids and Glycoproteins

Figure 11:
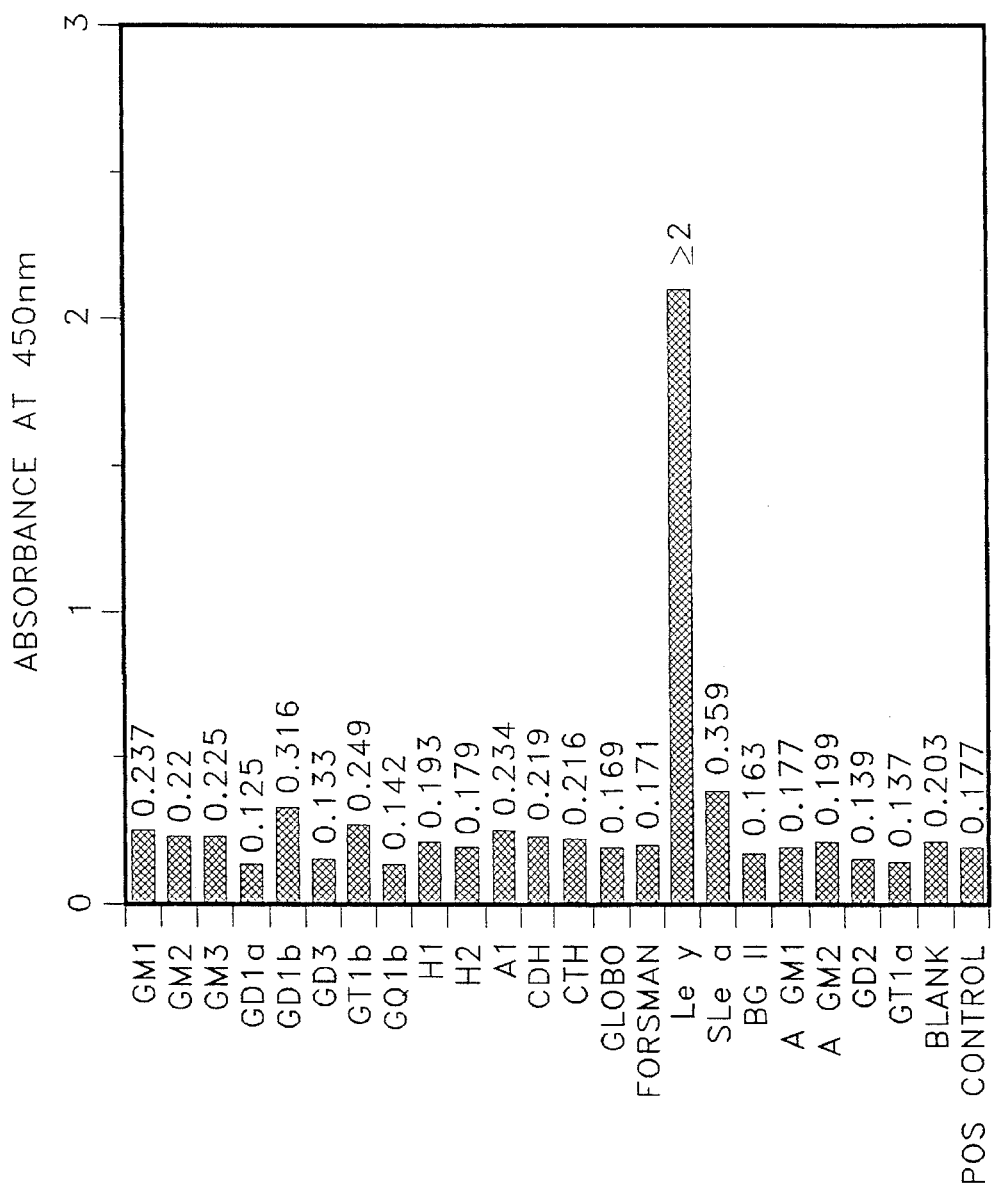
FIG. 11 is a bar graph of the results of testing the reactivity of BR96 against glycolipids as described in Example 7, infra.
Figure 12:
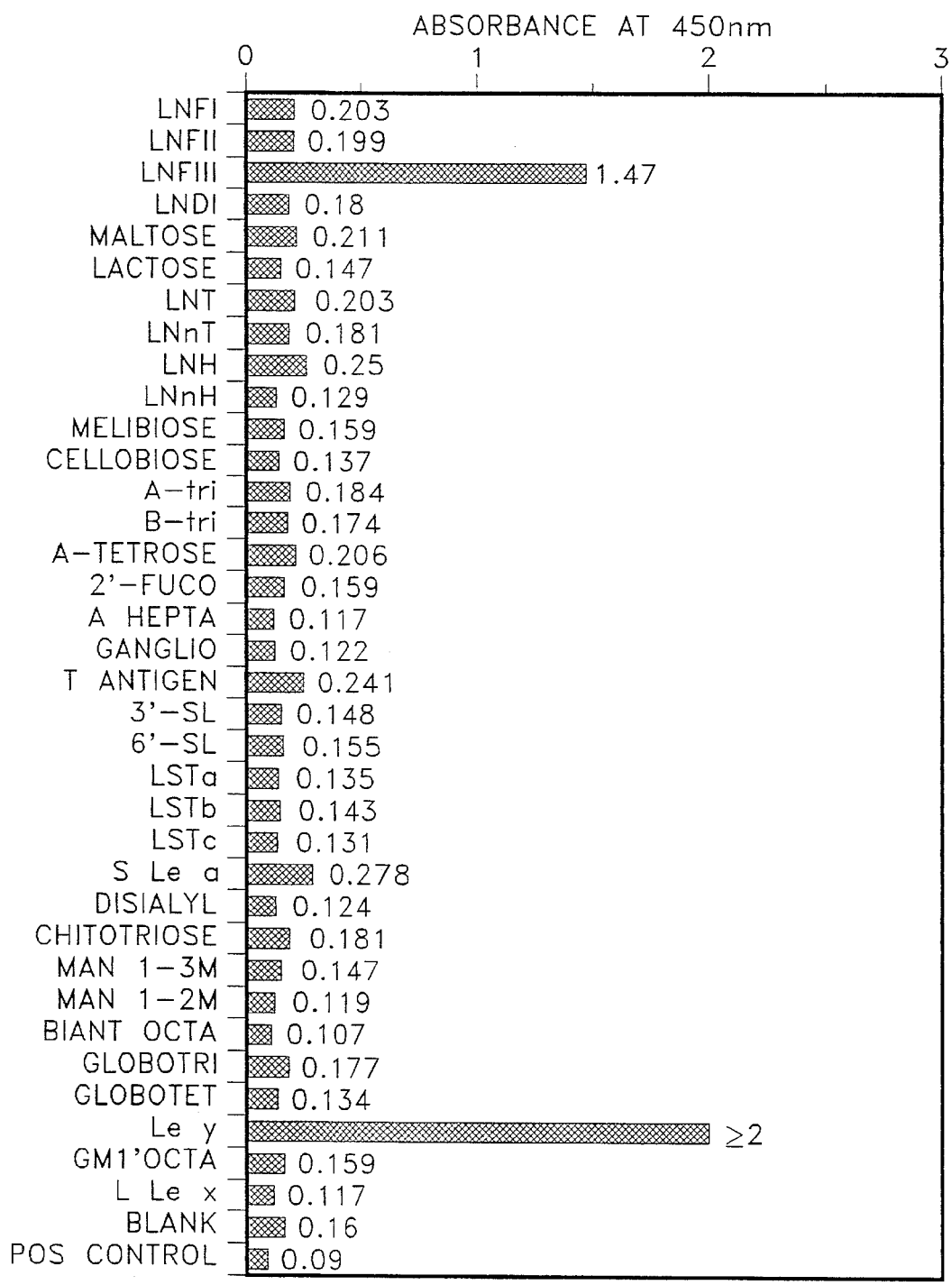
FIG. 12 is a bar graph of the results of testing the reactivity of BR96 against neoglycoproteins as described in Example 7, infra.

BR96 antibody was tested for reactivity to a variety of immobilized glycolipid antigens having known carbohydrate structures and syntheticglycoproteins (so called "neoglycoproteins") using an ELISA assay in which purified glycolipids and glycoproteins and antibody were used in excess (Dr. John Magnani, Biocarb, Gaithersburg, Md.; Lloyd et al., *Immunogenetics* 17:537–541 (1983)). Glycolipids were dried from methanol in microliter wells at 100 ng/well. Synthetic glycoproteins were coated on the surface of the wells by incubation of glycoprotein diluted to 200 ng in phosphate buffered saline (PBS), at pH 7.4/well. Purified BR96 was assayed at a concentration of 10 μg/ml in 0.01M Tris-HCl, pH 7.4, containing 1% BSA containing 1% bovine serum albumin and antibodies from ascites were assayed at a dilution of 1:100 in the same buffer. At these high concentrations most binding interactions are readily detected. Absorbance values were calculated as the average of duplicate wells. The results of this analysis are summarized in FIGS. 11 and 12 showing that BR96 reacted with Le$^y$ antigen.

These findings indicate that BR96 can bind to a variant form of the Lewis Y (Fuc α1-2Galβ1-4(Fucα1-3) GlcNAc. antigen and that fucose α1-3 attached to GlcNAc forms a portion of the Le$^{11c}$-related epitope recognized by BR96. The high tumor specificity of BR96 and ability to internalize (not previously described for monoclonal antibodies reactive with Le$^y$ antigens) suggests that the antibody recognizes a complex epitope, a portion of which includes the Le$^y$ antigen.

EXAMPLE 8

Preparation and Characterization of BR96 F(ab')$_2$ Fragments

Murine BR96 (IgG$_3$) was purified by Protein A affinity chromatography from murine ascitic fluid. Briefly, delipidated ascites was passed over a column containing a matrix of immobilized Protein A (RepliGen Corp., Cambridge, Mass.) previously equilibrated with 1M potassium phosphate, pH 8.0. Following the passage of ascites, the column was washed with equilibration buffer until no further protein was spectrophotometrically detected. The bound BR96 was then eluted from the column using 0.1M citrate buffer, pH 3.0. Immediately after elution, the eluate was neutralized with 1.0M Tris buffer, pH 9.0, until the pH was approximately 7.0. The monoclonal antibody was then dialyzed into PBS and concentrated prior to storage or use.

F(ab')$_2$ fragments were then generated by digesting purified BR96 monoclonal antibody with pepsin according to Lamoyi, "Preparation of F(ab')$_2$ Fragments from Mouse IgG of Various Subclasses", *Meth. Enzymol.* 121:652–663 (1986). Residual whole antibody and Fc fragments were adsorbed from the reaction mixture by passage over a protein A affinity column. The resulting F(ab')$_2$ fragment preparations were dialyzed extensively against PBS and sterile filtered.

The BR96 F(ab')$_2$ fragments preparations were characterized by gel permeation HPLC, SDS-PAGE and by ELISA on the human breast tumor line 3396 (Oncogen, Seattle, Wash.). Gel permeation HPLC was used to assess the molecular sizes of the proteins comprising the F(ab')$_2$ preparation. Reproducible chromatograms from different preparations indicated that 75–80% of the protein was F(ab')$_2$. No protein was detected at the positions representing higher molecular weight material, such as whole BR96 or protein aggregates. The remaining 20–25% of the protein eluted at positions corresponding to inactivated pepsin and to other smaller non-protein A-binding digestion products.

Nonreducing and reducing SDS-PAGE was used to examine the denatured molecular sizes and structural arrangement of the proteins in the F(ab')$_2$ preparations. A single major band at the position of F(ab')$_2$ (approximately 100 kdal) was typically observed, with no visible contaminating whole monoclonal antibody band (160 kdal). Lower molecular weight bands (i.e. less than 100 kdal) representing inactivated pepsin and small digestion products were minimal. Under reducing conditions the expected results were obtained with the only major bands occurring as a doublet at approximately 25 kdal representing the light chain and the remaining fragmented portion of the heavy chain. No whole heavy chain band was observed.

Figure 13:
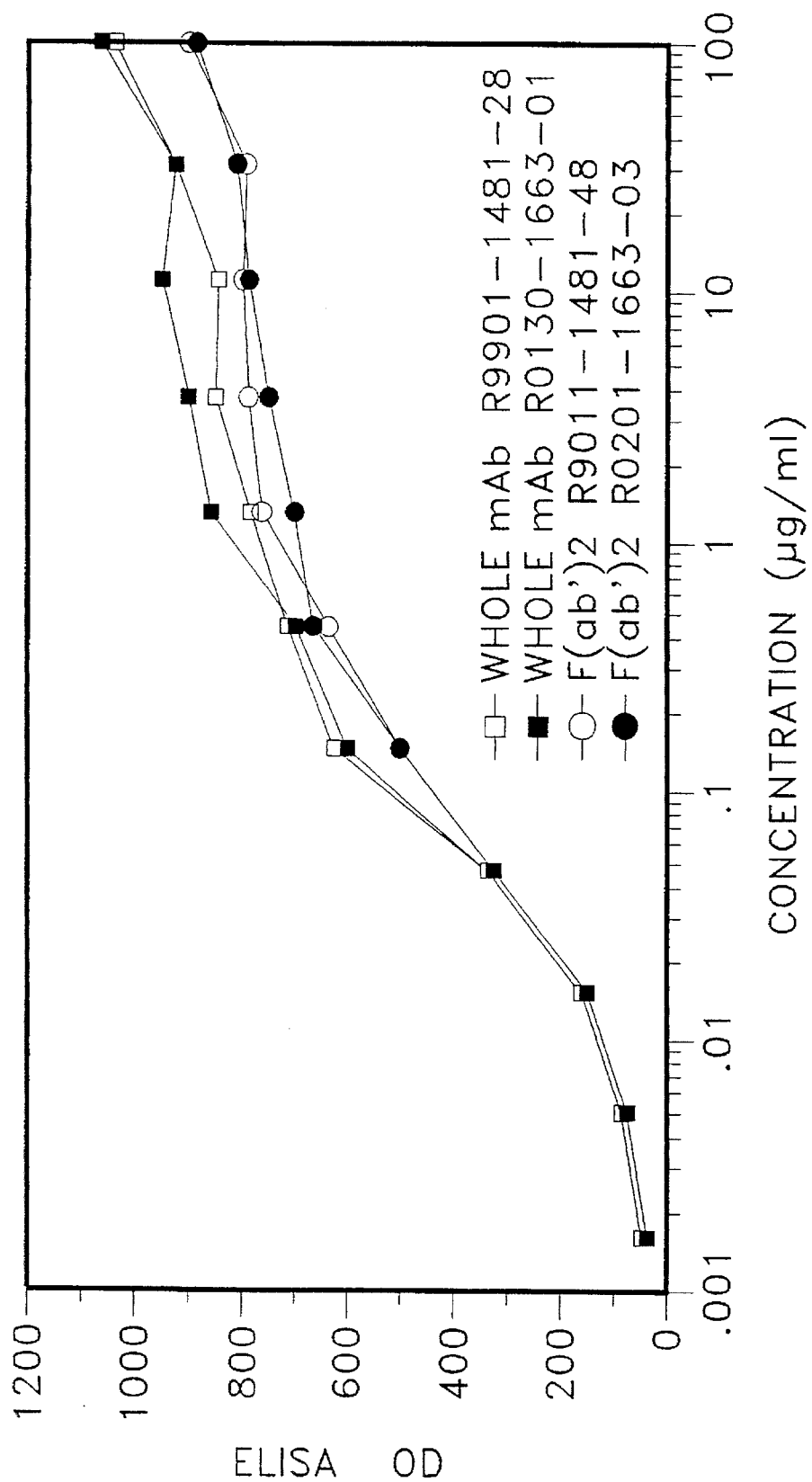
FIG. 13 is a graph of the binding activity of BR96 F(ab')$_2$ fragments compared to that of whole BR96 monoclonal antibody in an ELISA using goat anti-K light chain detecting reagent, as described in Example 8, infra.
Figure 14:
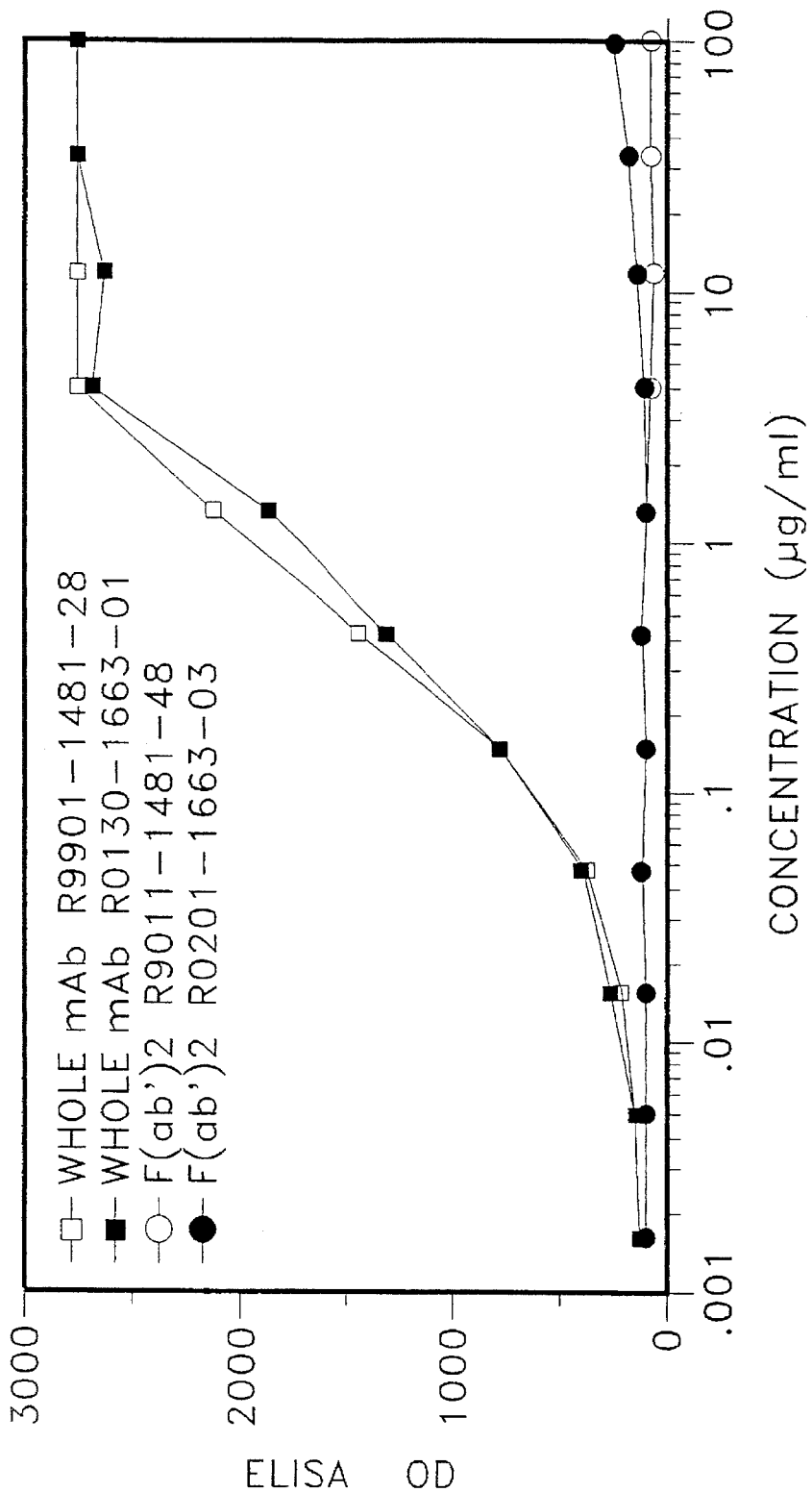
FIG. 14 is a graph of the binding activity of BR96 F(ab')$_2$ fragments as compared to that of whole BR96 monoclonal antibody in an ELISA using peroxidase conjugated protein A detecting reagent, as described in Example 8, infra.

Functional (binding) activity of the BR96 F(ab')$_2$ fragments was compared to that of whole BR96 in an ELISA with 3396 cells supplying the antigen. Binding of BR96 whole antibody or F(ab')$_2$ fragments to the cells was detected with an HRP-conjugated goat anti-murine K light chain reagent as shown in FIG. 13. On a duplicate plate, binding of whole BR96 was distinguished from binding of F(ab')$_2$ fragments by using HRP-conjugated protein A which binds to the whole antibody but not the F(ab')$_2$ fragments (FIG. 14).

These results indicate that BR96 F(ab')$_2$ (lot R0201-1663–03, lot 2) contained a trace amount of whole BR96 antibody. The level of contaminating whole antibody can be estimated to be approximately 8 trifold dilutions away from the amount of F(ab')$_2$ present, or about 0.01%. The other F(ab')$_2$ preparation (lot R9011-1481-48, lot 1) showed no detectable level of contaminating whole BR96, indicating that any effect of BR96 can be explained by binding of the Fab region and not the Fc region.

In summary, the BR96 F(ab')$_2$ preparations appear to be completely free of contaminating whole BR96 IgG by HPLC and by SDS-PAGE. In only one instance, when a very sensitive ELISA method was used were detectable levels of contaminating whole BR96 antibody found and this represented only approximately 0.01% by weight compared to the amount of F(ab')$_2$ fragments present.

EXAMPLE 9

Preparation and Characterization of Chimeric BR96 Antibody (ChiBR96)

The murine/human chimeric BR96 antibody of the invention ("ChiBR96") was produced using a two-step homologous recombination protocol as described by Fell et al., in *Proc. Natl. Acad. Sci. USA* 86:8507–8511 (1989) and in co-pending patent application by Fell and Folger-Bruce, U.S. Ser. No. 243,873, filed Sep. 14, 1988, and Ser. No. 468,035, filed Jan. 22, 1990, and assigned to the same assignee as the present application; the disclosures of all of these documents are incorporated in their entirety by reference herein.

Human Heavy Chain DNA Transfection

Figure 15:
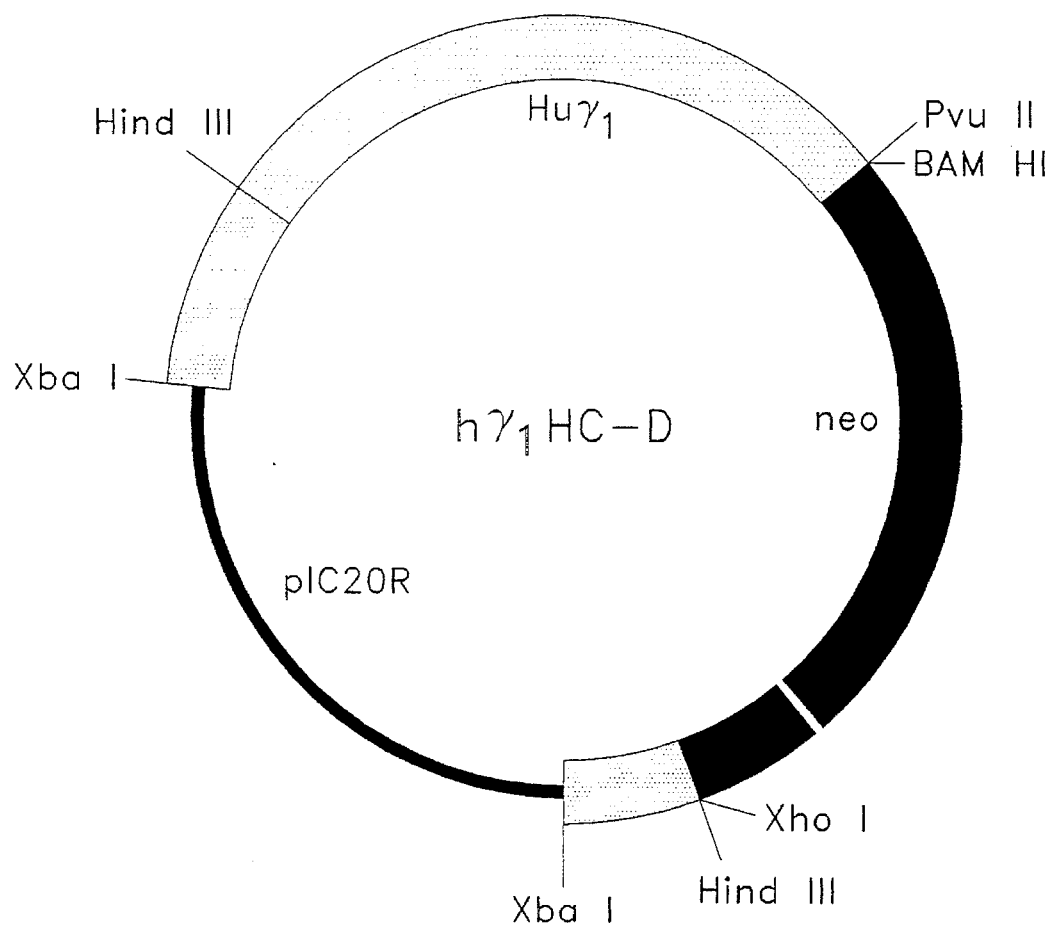
FIG. 15 is a diagram of vector phgamma$_1$HC-D used in the electroporation procedure, as described in Example 9, infra.

The murine hybridoma cell line BR96, ATCC No. HB10036, obtained as described above was transfected ($8\times10^6$ cells) with hgammal/HC-D (deposited at Agricultural Research Service Culture Collection (NRRL), Peoria, Ill., NRRL No. B 18599) (FIG. 15) by electroporation (Gene Pulser; Biorad Laboratories, Richmond, Calif.) at 250 V, 960 µFd capacitance setting, in isotonic phosphate buffered saline (PBS) and 30 µg/ml of the purified 6.2 kb Xba1 restricted fragment of the vector hgamma1HC-D. After 48 hr cells were seeded in 96-well plates at $10^4$ cells/well. Selection for Neo$^R$ was carried out in IMDM medium (GIBCO, Grand Island, N.Y.) containing 10% (vol/vol) fetal bovine serum (FBS) and the antibiotic aminoglycoside G418 (GIBCO) at 2.0 mg/ml.

Detection of Secreted Human IgG (Hu gammal) Antibody by ELISA

Culture supernatants were screened using a sandwich ELISA assay 2 weeks after transfection. Goat anti-human IgG, Fc specific (CALTAG, San Francisco, Calif.) was used as the capture antibody and goat αhuman IgG, Fc specific conjugated to horseradish peroxidase HRPO, (CALTAG) was the antibody used to detect bound human IgG. Cells from the HuIgG positive wells were subcloned by dilution and dilution clones were screened by ELISA to detect human IgGgammal by the previously described method. The clones containing human IgGgammal were also screened by ELISA to detect murine IgG3 heavy chain. Goat anti-mouse IgG3 (Southern Biotechnology Assoc., Inc., Birmingham, Ala.) was used as the capture antibody and goat anti-mouse conjugated to HRPO (Southern Biotechnology Assoc., Inc.) was the antibody used to detect the mouse IgG3.

One of the human IgGgammal positive murine IgG3 negative (Hugamma1$^+$, MUG3$^-$) clones was chosen and designated ChiHBR96. This heavy chain chimeric hybridoma cell line, ChiHBR96 was characterized for antigen specificity on MCF-7 cells and for expression levels by a quantitative ELISA for human IgG expression on MCF7 cells. The cell line ChiHBR96 expressed approximately 20 µg/ml of antigen-specific human IgG antibody.

Light Chain DNA Transfection

Figure 16:
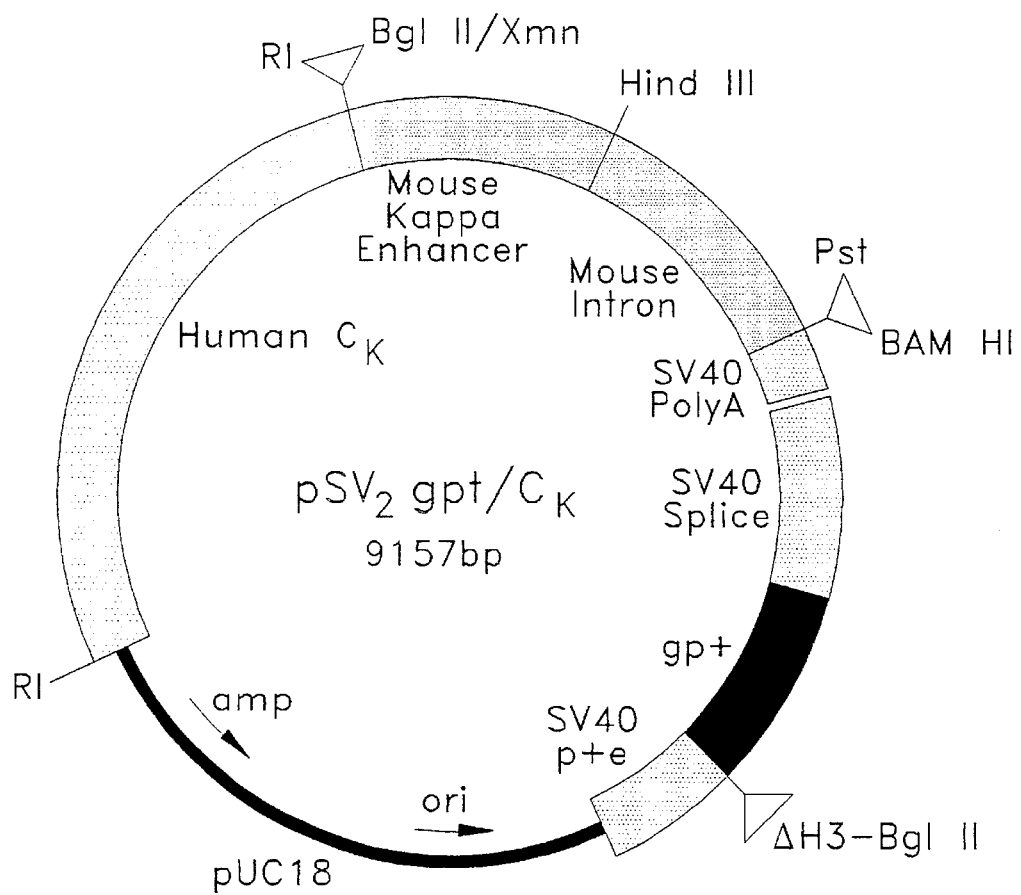
FIG. 16 is a diagram of vector pSV$_2$gpt/C$_K$ used in the electorporation procedure, as described in Example 9, infra.

The ChiHBR96 hybridoma ($8\times10^6$ cells) was transfected by electroporation as described above but using 30 µg/ml of the human light chain recombination vector pSV$_2$gpt/C$_K$ (NRRL No. B 18507) containing the human light chain K immunoglobulin sequence shown in FIG. 16, linearized with HindIII. After 48 hr cells were seeded in 96-well plates at $10^4$ cells/well. Selection for gpt was carried out in IMDM medium containing 10% (vol/vol) FBS, 15 µg/ml hypoxanthine, 250 µg/ml xanthine and 2.25 µg/ml mycophenolic acid (MA).

Detection of Secreted Human Kappa (Hu K) Antibody by ELISA

Culture supernatants were screened using a sandwich ELISA assay as described above, 2 weeks after transfection. Goat α-human K (CALTAG) was the capture antibody and goat anti-human K HRPO (CALTAG) was the antibody used to detect bound human K. Wells containing human K antibody were subcloned by dilution and the clones were screened by ELISA to detect human K or murine K chain. Goat anti-mouse K (Fisher Scientific, Pittsburgh, Pa.) was used as the capture antibody and goat anti-mouse K conjugated to HRPO (Fisher Scientific) was the antibody used to detect the presence of the mouse K chain. One of the human K positive, murine K negative clones (HuK$^+$, MuK$^-$) was chosen to analyze antigen specificity on MCF-7 cells and for expression levels by a quantitative ELISA for human IgG expression on MCF-7 cells. A cell line that was antigen specific for MCF-7 cells and HuIgG$^+$, MuIgG3$^-$, HuK$^+$, MuK$^-$ was chosen and designated Chimeric BR96 (Chi-BR96).

The original expression of the heavy and light chain antigen specific chimeric BR96 (Chi-BR96) antibody was approximately 25 µg/ml. Through four sequential rounds of cloning the line in soft agarose with a rabbit α HuIgG antibody overlay to detect cells secreting the highest amount of chimeric antibody [Coffino et al., *J. Cell. Physiol.* 79:429–440 (1972)], a hybridoma cell line (ChiBR96) was obtained secreting approximately 130 µg/ml of chimeric antibody. Hybridoma ChiBR96 was deposited with the ATCC on May 23, 1990, and there provided with the deposit number, ATCC No. HB 10460.

Binding of ChiBR96

The relative affinity of the ChiBR96 antibody and murine BR96 antibody of the invention for the tumor associated antigen on MCF-7 cells was determined by an ELISA competition binding assay [Hellstrom et al., Cancer Res. 50:2449–2454 (1990)]. Briefly, adherent antigen bearing cell line MCF-7 was plated in a 96-well microtiter dish at $3 \times 10^4$ cells/well and allowed to grow to confluency for about 3–4 days. The growth media was discarded and the cells are fixed with 0.5% glutaraldehyde in PBS (Sigma Chemical Co., St. Louis, Mo.), at 100 µl/well for 30 min. The glutaraldehyde was discarded and the plate was washed gently with PBS three times. The plate was then blocked with binding buffer (0.1% BSA in DMEM) 200 µl/well for 1 hr or was stored indefinitely at −20° C. Binding buffer was discarded and samples and standards were added to the wells. The plates were covered and incubated overnight at 4° C. Samples and standards were discarded and the plates were washed three times with PBS. HRP-conjugate diluted in 1% horse serum in PBS was added to wells, 100 µl/well and incubated for 1 hr at 37° C. The ELISA was developed with 3,3',5,5'-tetramethyl-benzidine (TMB) chromagen (Genetic Systems, Seattle, Wash.) in a citrate buffer. Color development was arrested with 3N $H_2SO_4$ and the plate was read on a Titertek Microplate reader at 450 nm. This assay determined how well 0.3 µg/ml of biotinylated ChiBR96 antibody competes with either unlabeled ChiBR96 or unlabeled murine BR96 monoclonal antibody for the antigen. The bound biotinylated ChiBR96 antibody was detected with avidin-HRPO and developed with standard ELISA reagents.

Figure 17:
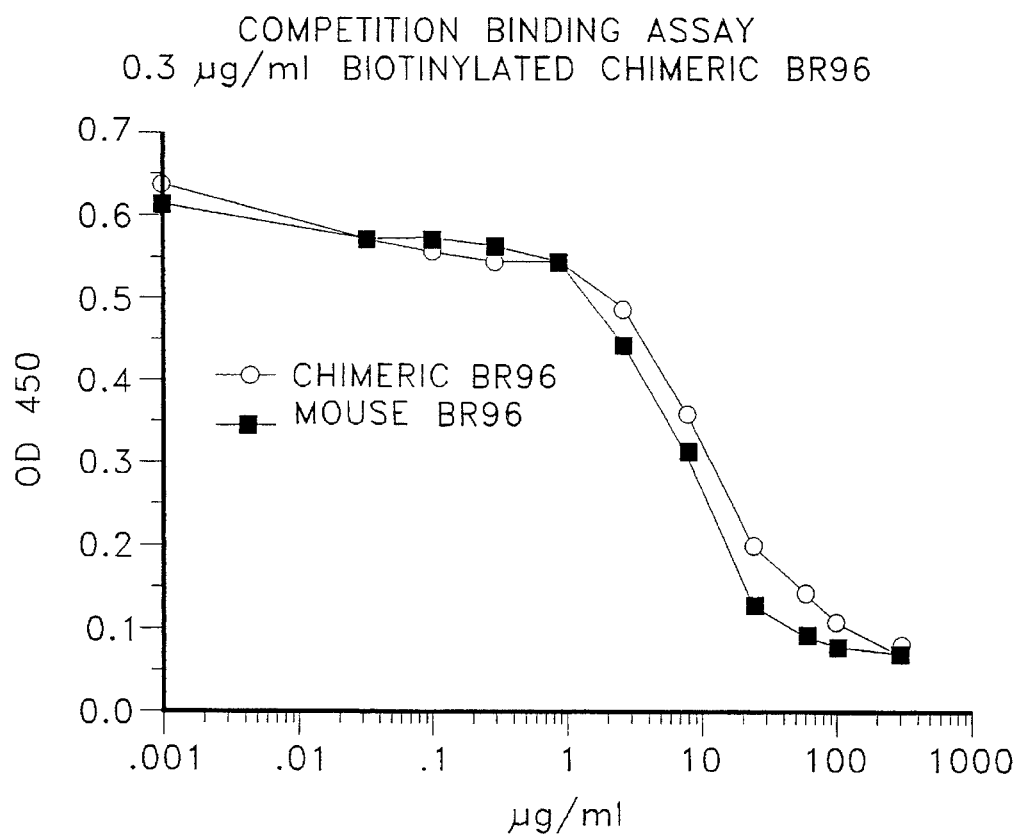
FIG. 17 is a graph depicting the results of the competition binding assay comparing the binding of the murine BR96 monoclonal antibody of the invention with binding of the chimeric BR96 antibody of the invention, as described in Example 9, infra.

As shown in FIG. 17, the overlap of the two binding curves indicates that the two antibodies have the same specificity and relative affinity for the tumor antigen.

EXAMPLE 10

Characterization of the ChiBR96 Antibody and BR96 F(ab')$_2$ Fragments

Cytotoxicity of Unmodified ChiBR96 and BR96 F(ab')$_2$ Fragments

Living suspended cells from the BR96 antigen positive carcinoma lines 3396, 2987 and MCF-7, were treated with ChiBR96 and BR96 F(ab')$_2$ fragments prepared as described in Examples 8 and 9, above, to determine cytotoxicity of these antibodies as compared to the BR96 monoclonal antibody of the invention. The cytotoxicity tests were performed by FACS assay as described above in Example 4. The results of these experiments are shown in FIGS. 18–20 as percentage dead cells vs. antibody concentration in µg/ml.

Figure 18:
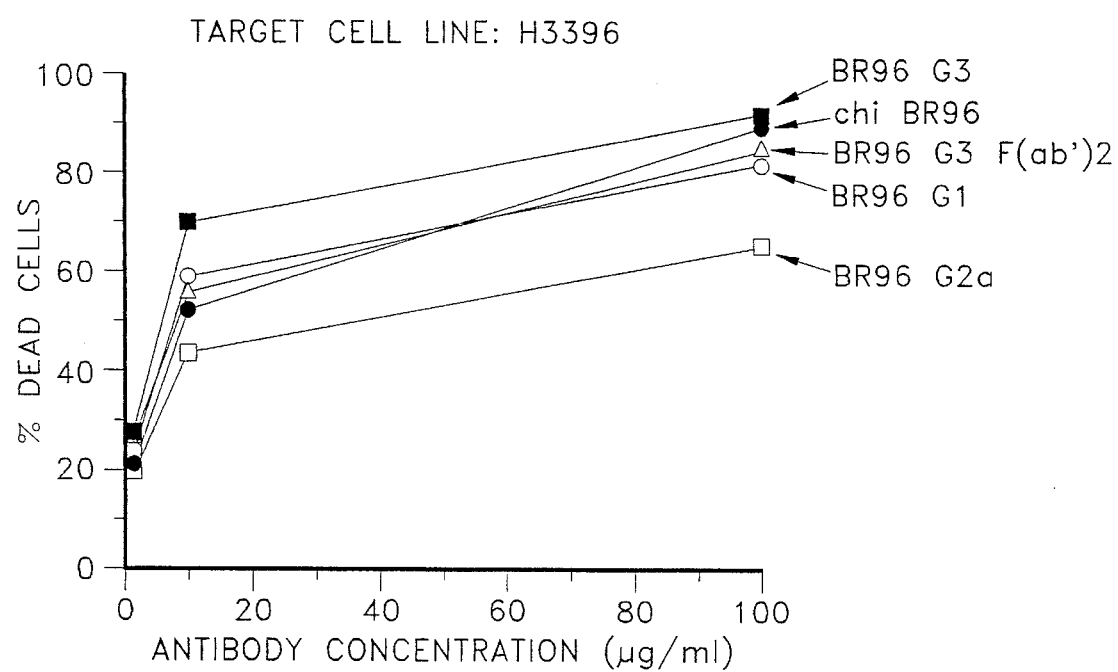
FIG. 18 depicts the results of FACS analysis of the cytotoxicity of the antibodies of the invention on 3396 breast carcinoma cells as described in Example 10, infra.
Figure 19:
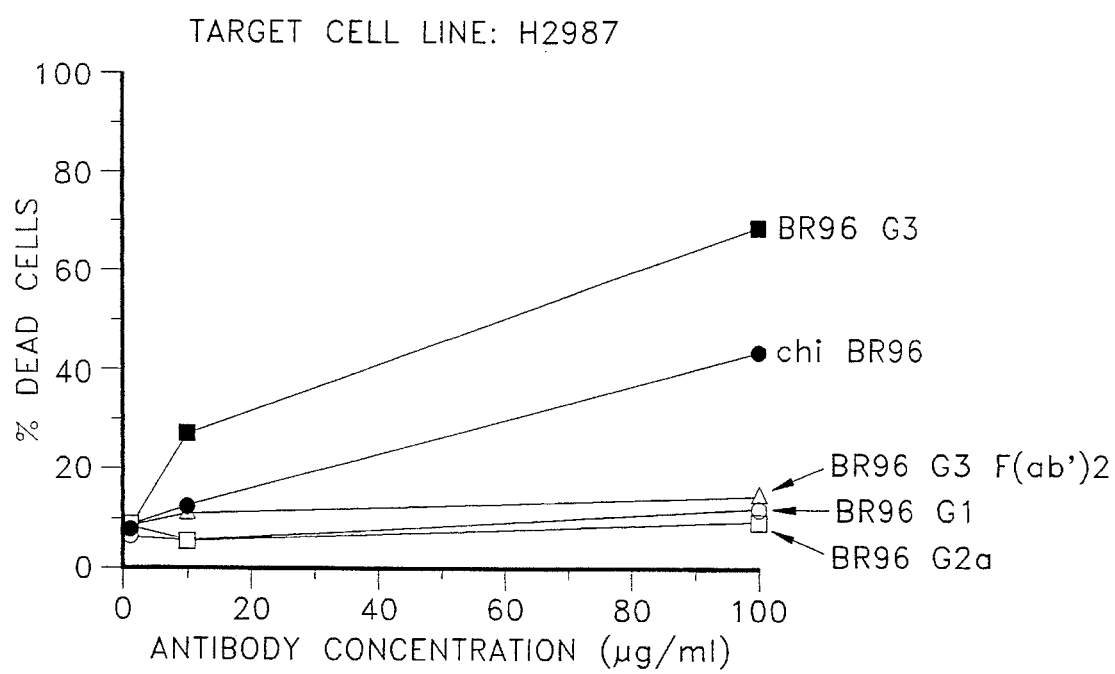
FIG. 19 depicts the results of FACS analysis of the cytotoxicity of the antibodies of the invention on 2987 human lung adenocarcinoma cells as described in Example 10, infra.
Figure 20:
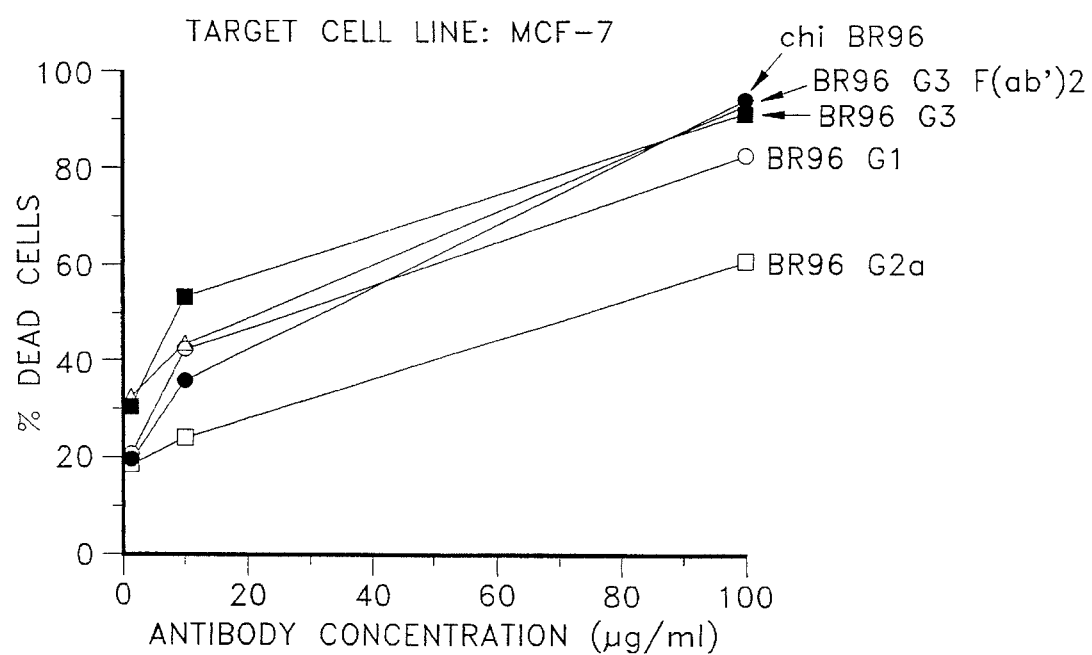
FIG. 20, depicts the results of FACS analysis of the cytotoxicity of the antibodies of the invention on MCF-7 cells as described in Example 10, infra.

FIGS. 18 and 20 show that the chimeric BR96 antibody and F(ab')$_2$ fragments of BR96 IgG3 are similar to BR96 monoclonal antibody with respect to cytotoxicity to 3396 and MCF-7 cells. FIG. 19 demonstrates that the cytotoxic effect on 2987 cells is much lower than on the other breast carcinoma cells (FIGS. 18 and 20). These results suggest that a higher binding ratio (Table 2) is important for killing by these antibodies and/or that different tumor cells might have different sensitivity to killing by these antibodies. These results illustrate that the ChiBR96 antibody and the F(ab')$_2$ fragments are cytotoxic by themselves, i.e. in unconjugated form, and also illustrate that the cytotoxicity of the BR96 antibodies is not dependent on the Fc region.

Internalization of ChiBR96

The internalization of the ChiBR96 antibody within carcinoma cells was evaluated in comparison to internalization of the BR96 monoclonal antibody. The antibodies were conjugated to ricin A chain toxin to form immunotoxins ChiBR96-RA (1–4 Ricin A chains per antibody molecule) and BR96-RA (1–2 Ricin A chains per antibody molecule) and internalization by carcinoma cell lines 3396 and 3630 was measured using a thymidine uptake inhibition assay, as described in Example 3, above.

Figure 21:
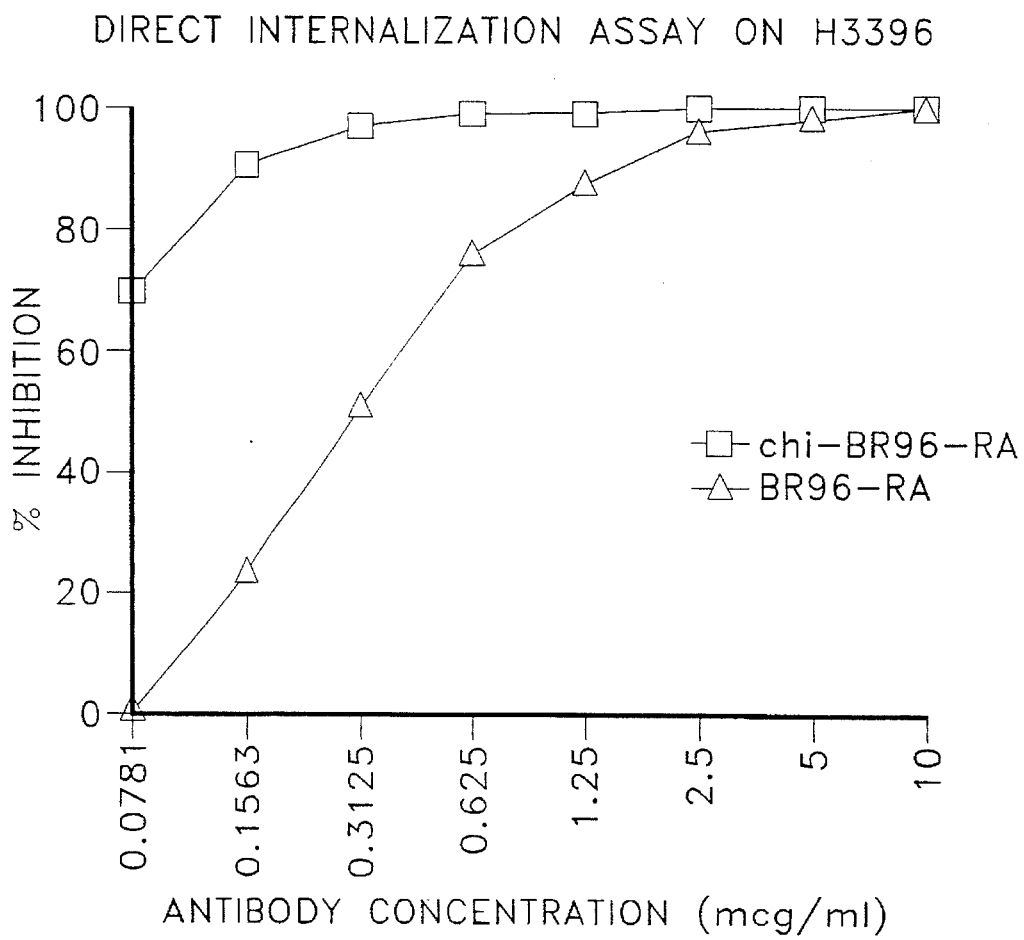
FIG. 21, depicts the percent inhibition of thymidine incorporation into the DNA of 3396 breast carcinoma cells treated with a murine BR96-RA immunotoxin and chimeric (Chi)BR96-RA at varying concentrations as described in Example 10, infra.
Figure 22:
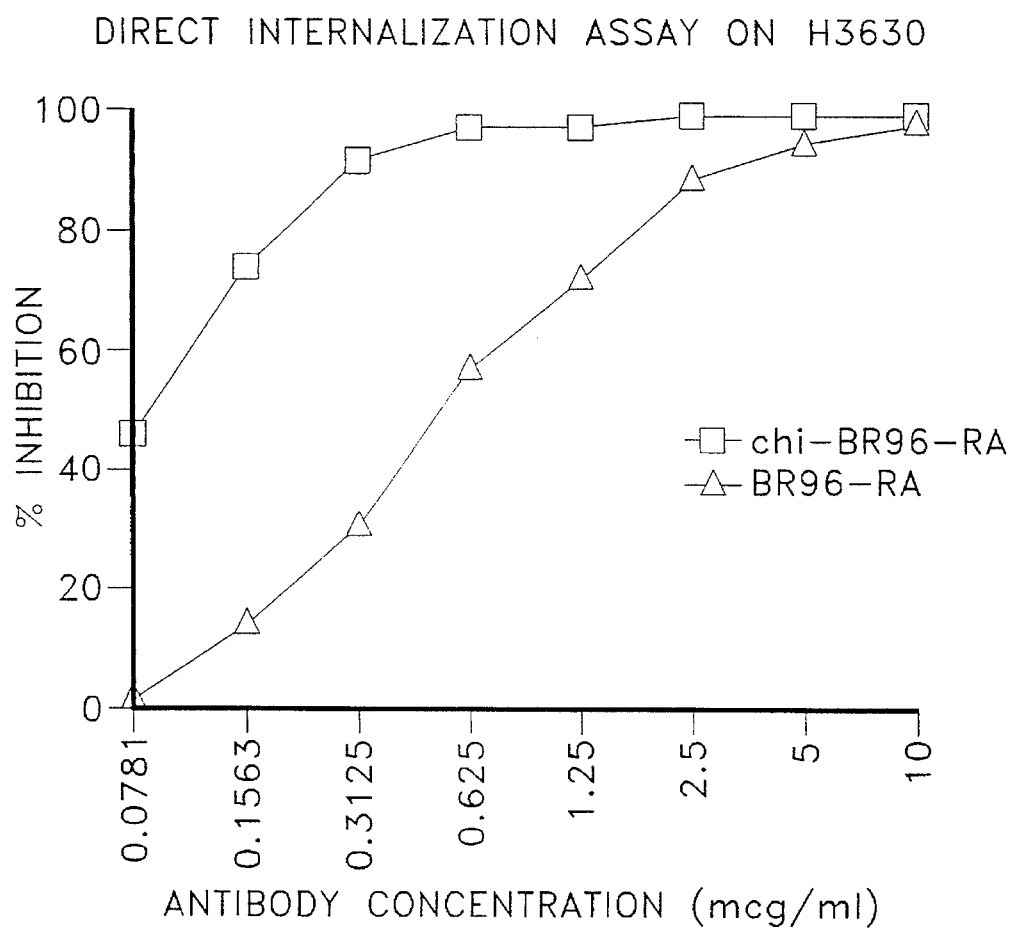
FIG. 22, depicts the percent inhibition of thymidine incorporation into the DNA of 3630 breast carcinoma cells treated with a murine BR96-RA immunotoxin and ChiBR96-RA at varying concentrations, as described in Example 10, infra.

Graphs of the percent inhibition of thymidine incorporation vs. immunotoxin concentration for each cell line tested are shown in FIGS. 21 and 22. FIG. 21 depicts the percent inhibition of thymidine incorporation by cells from the 3396 breast carcinoma cell line caused by internalization of ChiBR96-RA and BR96-RA. As shown in the graph, ChiBR96 is internalized similarly to BR96, and appears to be at least as efficient as BR96 at killing tumor cells. Similar results were obtained with the 3630 breast carcinoma cell line (FIG. 22).

ADCC Activity of ChiBR96 Antibody

Determination of ADCC activity of ChiBR96 was conducted as described in Example 5, above using the following cell lines: breast cancer lines 3396, 3630 and 3680 (Oncogen, Seattle, Wash.) and MCF-7 (ATCC No. HTB22); ovarian cancer line 3633-3 (Oncogen, Seattle, Wash.); and lung cancer lines 2987; 3655-3 and 2981 (Oncogen, Seattle, Wash.). The results are shown in Table 3 for various antibody concentrations.

TABLE 3

ADCC Activity of ChiBR96

| Cell Lines | Antibody | NK | Antibody Concentration (µg/ml) | | | | |
| --- | --- | --- | --- | --- | --- | --- | --- |
| | | | 10 | 1 | 0.1 | 0.01 | 0.001 |
| Breast Cancer | BR96 | 28 | 86 | 74 | 58 | 27 | 25 |
| 3396 | ChiBR96 | | 88 | 79 | 60 | 34 | 26 |
| MCF-7 | BR96 | 16 | 82 | 69 | 54 | 17 | 15 |
| | ChiBR96 | | 90 | 82 | 57 | 25 | 17 |
| MCF-7 | BR96 | 22 | 73 | 69 | 48 | 22 | 22 |
| | ChiBR96 | | 76 | 70 | 57 | 33 | 26 |
| 3630 | BR96 | 30 | 69 | 64 | 42 | 30 | 34 |
| | ChiBR96 | | 69 | 56 | 42 | 36 | 36 |
| 3680 | BR96 | 13 | 73 | 67 | 58 | 34 | 38 |
| | ChiBR96 | | 70 | 71 | 61 | 39 | 30 |
| Ovarian Cancer | BR96 | 20 | 92 | 90 | 64 | 28 | 23 |
| 3633-3 | ChiBR96 | | 88 | 88 | 54 | 43 | 29 |
| Lung Cancer | BR96 | 11 | 51 | 57 | 41 | 9 | 7 |
| 2987 | ChiBR96 | | 69 | 65 | 51 | 28 | 15 |
| 3655-3 | BR96 | 4 | 49 | 37 | 0 | 0 | 0 |
| | ChiBR96 | | 39 | 35 | 12 | 6 | 5 |
| 2981 | BR96 | 3 | 4 | 3 | 3 | 4 | 5 |
| | ChiBR96 | | 5 | 4 | 3 | 4 | 4 |

The results shown in Table 3 for various antibody concentrations indicate that ChiBR96 mediates ADCC activity to a similar extent as BR96. The ADCC activity can be seen at antibody concentrations lower than those at which the ChiBR96 antibody is cytotoxic by itself. When antibody BR96 was used alone as a control it produced 0% killing at the concentrations tested. ADCC activity was only found with the BR96 antibody-binding cell lines.

Ability of ChiBR96 to Mediate Complement-Mediated Cytotoxicity

Determination of the ability of ChiBR96 to kill tumor cells in the presence of human serum as a source of complement (CDC) were performed as described in Example 6, using breast cell lines 3396; MCF-7, 3630 and 3680; ovarian cancer cell line 3633-3; and lung cancer cell lines 3655-3, 2987 and 2981. Table 4 presents the results.

TABLE 4

CDC Activity of ChiBR96

| Cell Lines | Antibody | Antibody Concentration (μg/ml) | | | |
|---|---|---|---|---|---|
| | | 10 | 1 | 0.1 | 0.01 |
| Breast Cancer | BR96 | 100 | 99 | 78 | 13 |
| 3396 | ChiBR96 | 86 | 92 | 13 | 2 |
| MCF-7 | BR96 | 94 | 100 | 63 | 2 |
| | ChiBR96 | 92 | 83 | 1 | 0 |
| 3630 | BR96 | 94 | 100 | 82 | 9 |
| | ChiBR96 | 86 | 86 | 33 | 9 |
| 3680 | BR96 | 100 | 100 | 19 | 7 |
| | ChiBR96 | 87 | 100 | 5 | 9 |
| Ovarian Cancer | BR96 | 98 | 98 | 21 | 0 |
| 3633-3 | ChiBR96 | 100 | 100 | 26 | 1 |
| Lung Cancer | BR96 | 91 | 22 | 0 | 0 |
| 3655-3 | ChiBR96 | 46 | 3 | 0 | 0 |
| 2987 | BR96 | 100 | 100 | 1 | 0 |
| | ChiBR96 | 100 | 43 | 0 | 0 |
| 2981 | BR96 | 0 | 3 | 3 | 2 |
| | ChiBR96 | 1 | 1 | 2 | 10 |

As shown in Table 4, ChiBR96 gave a cytotoxic effect (CDC) similar to that of BR96, in the presence of human serum containing complement. BR96 and ChiBR96 were not cytotoxic in any concentration. Human serum was also not cytotoxic.

The above results demonstrate that the whole BR96 antibody and chimeric antibody of the invention are internalized within carcinoma cells to which they bind, are cytotoxic alone in unmodified form and have ADCC and CDC activity for cells expressing a higher amount of epitopes.

EXAMPLE 11

Evaluation of BR96 Antibodies In Vivo

The therapeutic potential of the unmodified BR96 antibody of the invention for treatment of tumors was examined in a series of experiments using human tumor xenografts in nude mice. In addition, certain parameters were examined that might influence the efficacy of BR96 as an antitumor agent. These parameters include level of antigen expression on the target tumor line, time from tumor implantation to initiation of therapy and effects of dose.

In all the in vivo experiments, the required number of Balb/c nu/nu mice (Harlan Sprague Dawley, Indianapolis, Ind.) were implanted with either the human lung adenocarcinoma cell line H2987 or H2707 tumor line. Cells from these tumor lines were grown in vitro, harvested, washed and resuspended in PBS prior to subcutaneous (s.c.) implantation of 10 million cells into the rear flank of each mouse. These groups of mice were then randomized and separated into smaller equal groups of 8 or 10 mice each.

To increase the chance of observing any antitumor effects of BR96 while still requiring the antibody to actually localize to the tumor implant site for any effect to occur, therapy was initiated 24 hours after tumor implantation on day 2. Both the BR96 and control MAbs were administered at the same dose and schedule, although initiation of therapy in some cases varied. The treatment dose was administered in 0.2 ml PBS intravenously (i.v.) through the tail vein of the mouse. Normally the schedule was once every three days for five injections (Q3DX5). However, two extra injections were given on days 19 and 21 after H2987 tumor implantation in the initial experiment.

Antitumor Effects of BR96 Antibody in 2987 and 2707 Tumors

Tumor volumes were determined for each animal weekly with measurement usually beginning on the eighth day after implantation. Tumor volumes were calculated from the measurements of tumor length and perpendicular width using the formula:

$$\text{Tumor Volume} = \text{longest length} \times (\text{perpendicular width squared}/2)$$

Group mean values were then calculated and plotted against time after tumor implantation.

Figure 23:
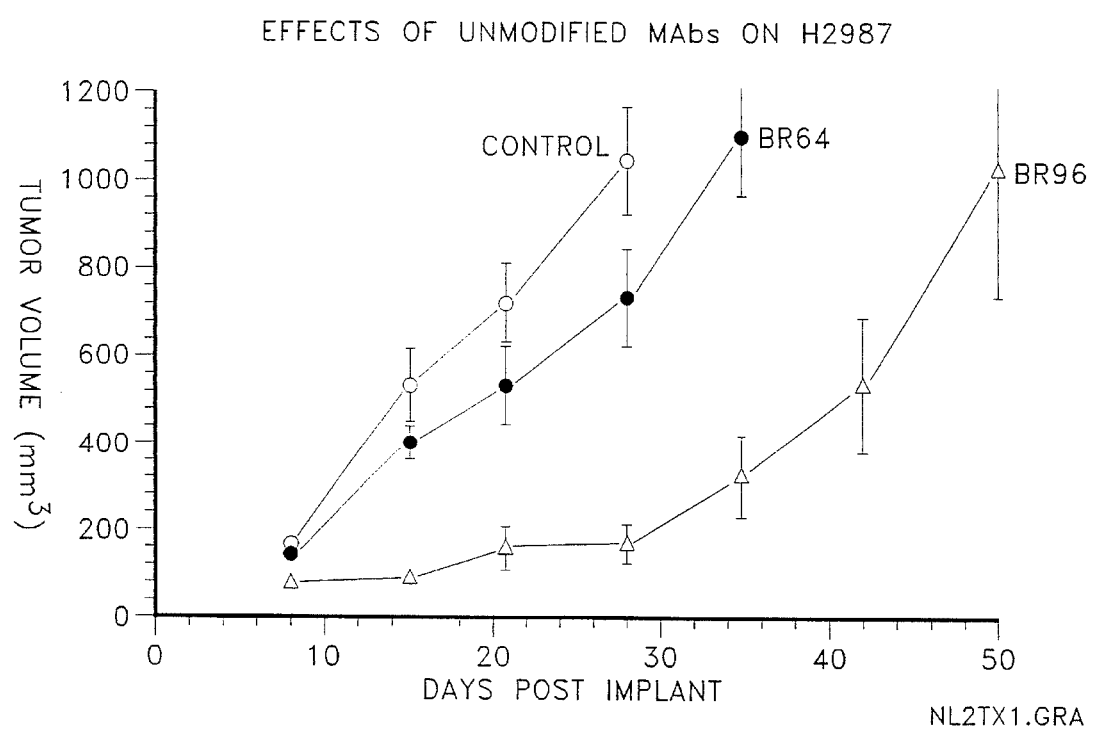
FIG. 23, is a graph depicting the antitumor effects of unmodified BR96 on the tumor cell line H2987, as described in Example 11, infra.

In the initial experiment depicted in FIG. 23 treatment with BR96 resulted in highly significant anti-tumor effects against the H2987 cell line. BR64, which also binds and is internalized by these cells, was used as a negative control, and showed little if any effect compared to the PBS treated controls.

Table 5 summarizes the effects on the individual tumors at the end of treatment in this first experiment.

TABLE 5

Effects of Treatment with Unmodified BR96 Initiated
At Different Times After H2987 Implantation
EXPERIMENT 1
DAY 28

| | | TUMOR RESPONSE | | | |
|---|---|---|---|---|---|
| GROUP | MAb | COMPLETE | PARTIAL | STABLE | PROGRESSION |
| 1 | BR96 | 2 | 0 | 3 | 5 |
| 2 | BR64 | 0 | 0 | 1 | 9 |
| 3 | PBS | 0 | 0 | 0 | 10 |

Only treatment with BR96 antibody resulted in complete absence of tumor. Two animals in this group were tumor free and an additional 3 animals showed cessation of growth of their tumors following treatment with BR96 antibody. The two mice showing no signs of tumor remained tumor free throughout the course of the experiment.

Antitumor Effects of BR96 Antibody on Established Tumors

One of the ultimate goals of tumor therapy is the effective treatment of established and growing tumors. To examine whether BR96 could have an antitumor effect on established tumors the H2987 or H2707 lung adenocarcinoma tumor lines were used as xenografts in nude mice. Because both of these tumor lines result in palpable tumors eight days after administration of 10 million cells s.c., delaying initiation of treatment provided a method to examine antitumor effects on established tumors.

Therefore, to further examine the efficacy of unmodified BR96, several experiments were performed where treatment was withheld for either 5 or 8 days following s.c. tumor implantation. The delay in treatment initiation allowed the tumor cells to become established tumors. This results in an animal model that is more difficult to treat but resembles the clinical situation in a more realistic manner.

The treatment protocol is summarized in Table 6. Three groups of 10 mice each were treated with BR96 antibody initiated at different times as described in this Table. Control mice received either FA6 or PBS beginning on DAY 2. FA6 is a murine $IgG_3$ directed against a bacterial antigen not found in mammalian species, and acted as an isotype matched nonbinding negative control monoclonal antibody.

TABLE 6

Effects of Treatment With Unmodified BR96
Initiated at Different Times After H2987 or
H2707 Implantation
TREATMENT PROTOCOL

| GROUP | MAb | SCHEDULE/ ROUTE | DOSE | DAYS INJECTED |
|---|---|---|---|---|
| 1 | BR96 | Q3DX5 i.v. | 1 mg | 2, 5, 8, 11, 14 |
| 2 | BR96 | Q3DX5 i.v. | 1 mg | 5, 8, 11, 14, 17 |
| 3 | BR96 | Q3DX5 i.v. | 1 mg | 8, 11, 14, 17, 20 |
| 4 | FA6 | Q3DX5 i.v. | 1 mg | 2, 5, 8, 11, 14 |
| 5 | PBS | Q3DX5 i.v. | 0.2 ml | 2, 5, 8, 11, 14 |

Figure 24:
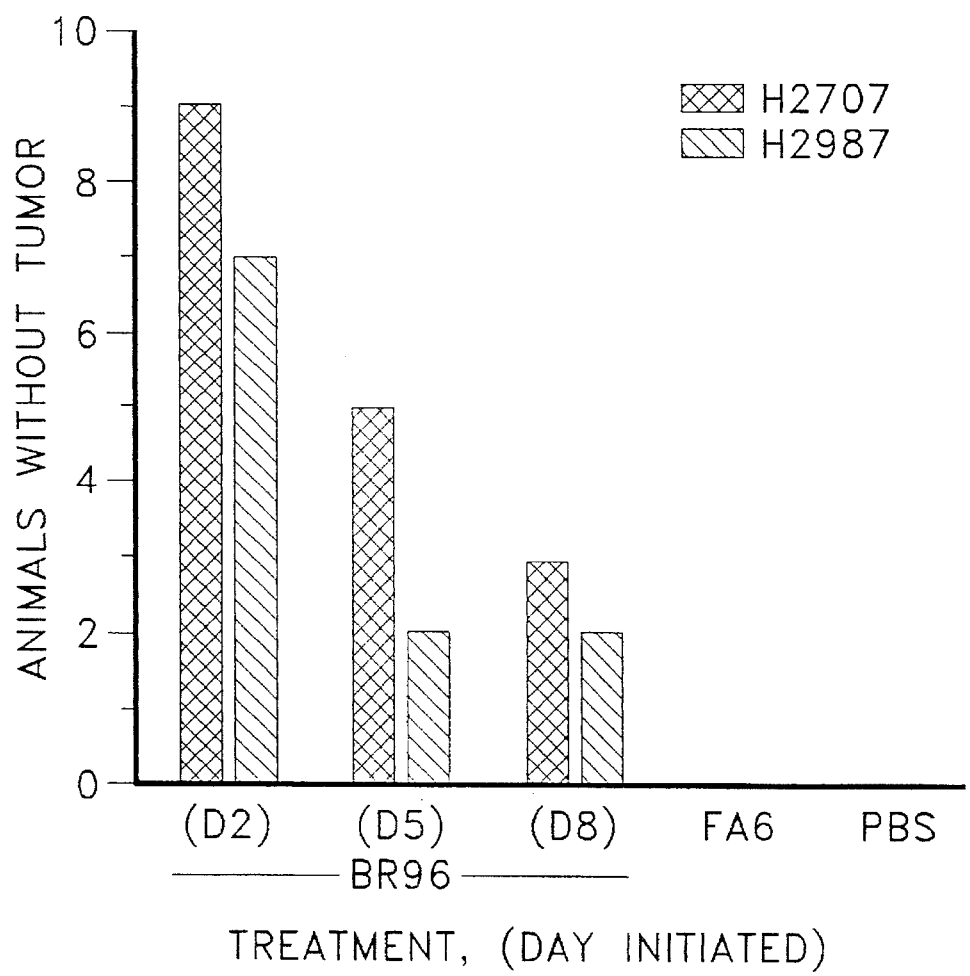
FIG. 24, is a bar graph illustrating the absence of tumors at the end of treatment for animals treated with BR96, as described in Example 11, infra.

The results of this treatment protocol for both H2987 and H2707 tumor cell lines are shown in FIG. 24, where the number of animals without tumors versus when initiation of treatment after tumor implantation occurred are plotted. Absence of tumor, as defined by the absence of a palpable tumor, was assessed at the end of treatment for each group. The day used for the determination of tumor absence varied since treatment was initiated at different times post tumor implant. Early initiation of treatment was clearly more effective and efficacy decreases as onset of treatment increased from time of tumor implant. Since delay in initiation of treatment allows greater growth and establishment of the tumor, decreased efficacy at later treatment initiation times reflects the increasing difficulty of treating larger and more established tumors.

These results demonstrate that BR96 has antitumor effects against two different tumor cell lines. Antitumor effects were only observed in the three groups treated with BR96 antibody while those animals treated with either the control FA6 or PBS showed no antitumor effects.

It is significant that the differences in efficacy with more established tumors are greater with the higher antigen expressing tumor line, H2707. The observation that H2707 has a greater response to BR96 therapy than H2987 is consistent with the assumption that the amount of antigen expressed by a tumor cell may influence the efficacy of BR96 treatment. From the data above it is clear that BR96 has antitumor effects against staged tumors.

Dose Effects of BR96 Antibody

Figure 25:
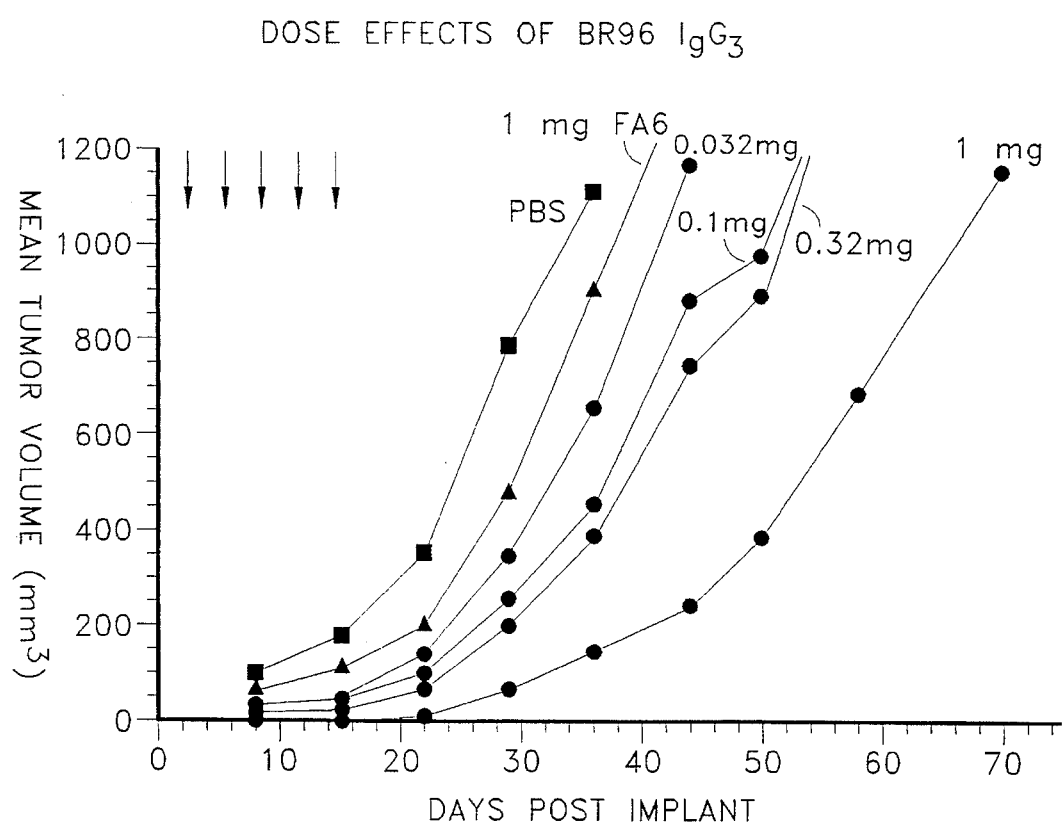
FIG. 25, depicts the dose effects of BR96 antibody after implantation of H2707 cells, as determined by tumor volume, as described in Example 11, infra.

In another experiment, the dose effects of BR96 against the H2707 tumor line was examined. In this experiment, BR96 was administered in decreasing half log amounts from 1 mg/dose to 0.032 mg/dose. The mean tumor volumes versus time post tumor implant of the groups are presented in FIG. 25. The control treated animals were given only the highest dose of monoclonal antibody, 1 mg/dose FA6. These control animals showed no antitumor effects while there was a dose dependent response when BR96 antibody was administered over the chosen dose range.

Antitumor Effects of F(ab')$_2$ Fragment and Chimeric BR96

Figure 26:
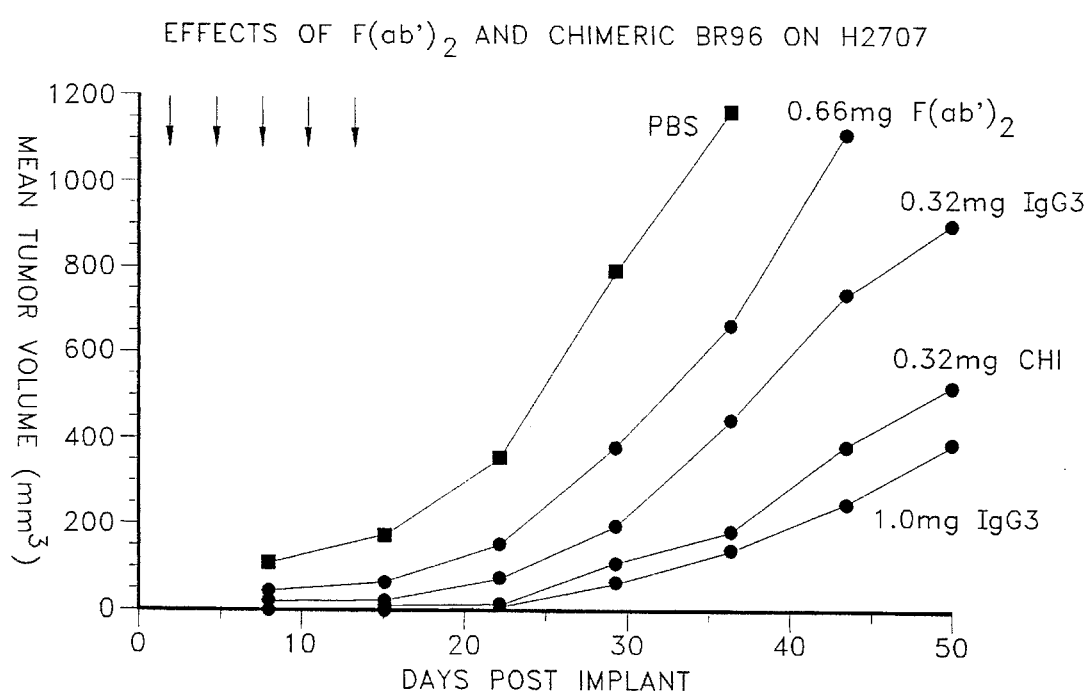
FIG. 26, illustrates the effects of treatment with F(ab')$_2$ fragments and Chimeric BR96 after implantation of 2707 cells as determined by tumor volume, as described in Example 11, infra.

In addition, antitumor effects of the F(ab')$_2$ BR96 fragment were examined to determine if the antitumor effects seen in vivo were due to the Fc portion or if actual binding to the tumor with its subsequent internalization was sufficient for the cell death, as indicated by in vitro assays. The dose of F(ab')$_2$ fragment was 0.66 mg/dose using the same schedule as the whole BR96. This dose corresponds to an approximate molar equivalent of binding regions compared to the 1.0 mg/dose whole IgG$_3$ BR96. Mean tumor volume values versus time post tumor implantation for this group treated with the antibody fragment are shown in FIG. 26. There were clearly some antitumor effects although the effects were not as strong as with whole antibody. These effects were most pronounced at the earlier time points during and immediately following treatment.

Chimeric BR96 was also examined for antitumor effects in this experiment. An intermediate dose of 0.32 mg/dose for the chimeric Mab was chosen. The mean tumor volume values for this group of mice is also shown in FIG. 26. Treatment with chimeric antibody BR96 was more efficacious than a comparable dose of the murine BR96 IgG$_3$. This is further demonstrated in FIG. 27 which shows that 6 of the 8 mice treated with chimeric BR96 were free of palpable tumors at the end of treatment.

Figure 27:
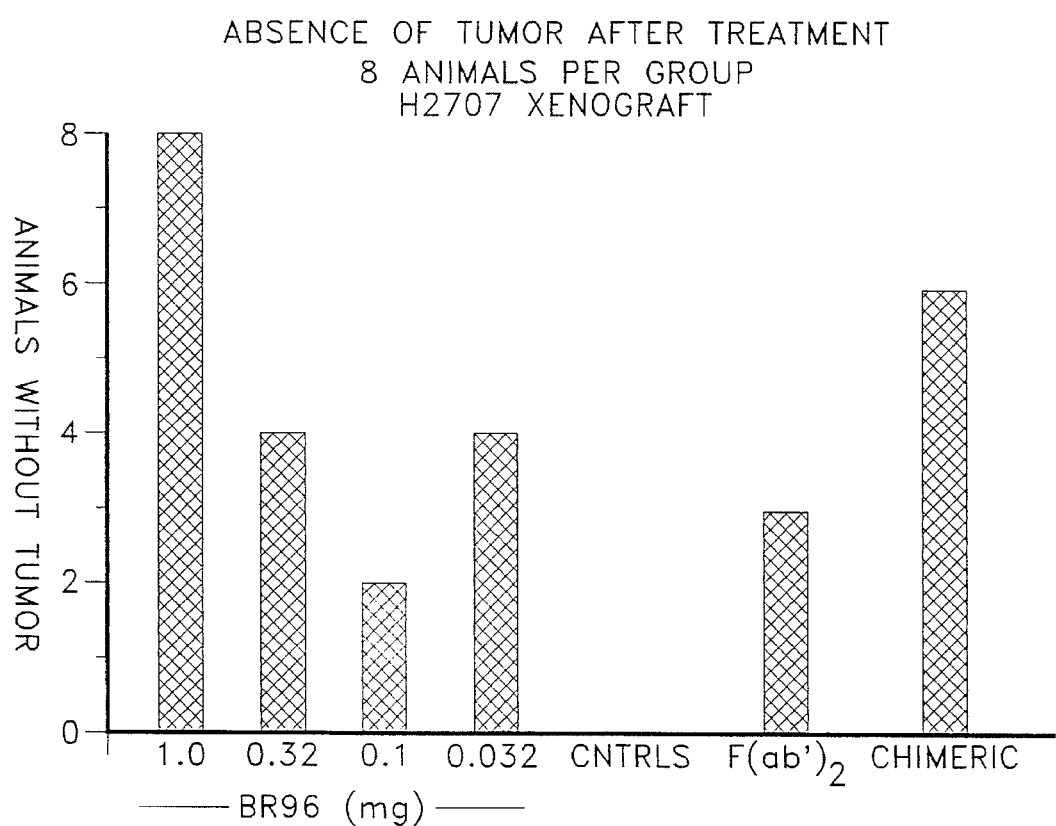
FIG. 27, illustrates the absence of tumors after treatment with various doses of BR96 antibody, as compared to the effects of F(ab')$_2$ fragments and Chimeric BR96, as described in Example 11, infra.

Examination of the individual tumors depicted in FIG. 27 shows that at completion of treatment a clear dose effect was evident by the number of animals without tumors after treatment with decreasing amounts of whole IgG$_3$ BR96 antibody from 1.0 to 0.1 mg/dose. Surprisingly, treatment with 0.032 mg/dose resulted in an antitumor effect similar to the 0.32 mg/dose. This may reflect that the level of cells killed in the tumor from the treatment was very close to the minimum amount necessary for the tumor to continue to grow.

Three of the eight animals treated with the F(ab')$_2$ fragment were free of palpable tumors after treatment. Therefore the Fc portion is not entirely necessary for the antibody to have antitumor effects in vivo although it should enhance the tumorcidal properties of BR96, particularly in immunocompetent animals.

The above demonstrates that unmodified BR96 antibodies are effective antitumor agents against tumor lines in vivo. Moreover, the BR96 antibodies have an effect on staged or established growing tumors. There is an indication that higher antigen density on the tumor line may increase the ability of BR96 to kill these cells. It has been shown that any of the forms of the monoclonal antibody, i.e., chimeric, murine whole IgG$_3$ or F(ab')$_2$ fragments, are effective as antitumor agents. Earlier treatment and higher doses are preferred.

EXAMPLE 12

Localization and Biodistribution of BR96 Antibodies

Radioiodinated BR96 monoclonal antibodies administered at doses used in the therapy experiments described above in Example 11, were used to determine biodistribution characteristics. Specifically, the whole IgG$_3$ BR96, chimeric or F(ab')$_2$ fragments together with the appropriate control (whole monoclonal antibody FA6, chimeric 96.5 and 96.5 F(ab')$_2$, respectively) were used to localize in the tumor and various other organs.

Prior to the localization experiments, animals were injected with tumor cells as described above in Example 11, for the therapy studies. However, the tumors were allowed to grow in the animals for approximately 2 weeks. At this time, 100 μg of BR96 antibody or fragment was radiolabeled with $^{125}$I using 10 μg Iodogen for 10 minutes at room temperature as directed by the manufacturer. Control antibody or fragments were labeled with $^{131}$I using the same method. These radioiodinated antibodies were diluted with the appropriate unlabeled antibodies to reach the doses used in the therapy experiments. Both the specific and nonspecific antibodies were then mixed and administered together, i.v., through the tail vein of the mouse. At selected times mice were randomly pulled from the group, anesthetized, bled through the orbital plexus and sacrificed. Various tissues were removed, weighed and counted on a gamma counter capable of differentiating between the two radioisotopes of iodine. From this data, percent injected dose and percent injected dose per gram were calculated.

The accumulated data from the 24 post administration time point in the localization experiments are summarized in Table 7.

TABLE 7

Summary of Biodistribution Experiments

| ANTIBODY | DOSE (mg) | TUMOR CELL LINE | % INJECTED DOSE/GRAM 24 HRS. POST ADMINISTRATION ||||||
|---|---|---|---|---|---|---|---|---|
| | | | BLOOD | TUMOR | LIVER | SPLEEN | KIDNEY | LUNG |
| 1) BR96-G$_3$ | 1.0 | H2987 | 10.2 | 6.8 | 2.2 | 1.9 | 3.4 | 4.7 |
| FA6 | 1.0 | | 6.3 | 2.1 | 2.1 | 1.6 | 2.4 | 3.2 |
| 2) BR96-G$_3$ | 0.3 | H2707 | 9.0 | 7.0 | 1.8 | 1.6 | 2.7 | 3.7 |
| FA6 | 0.3 | | 5.9 | 2.7 | 2.0 | 1.8 | 2.2 | 2.8 |
| 3) ChiBR96 | 0.32 | H2707 | 7.2 | 8.2 | 1.4 | 1.6 | 2.0 | 3.5 |
| Chi96.5 | 0.32 | | 7.5 | 2.3 | 1.8 | 1.6 | 1.9 | 3.5 |
| 4) F(ab')$_2$ | | | | | | | | |
| BR96 | 0.65 | H2707 | <0.3 | <0.3 | <0.3 | <0.3 | <0.3 | <0.3 |
| 96.5 | 0.65 | | <0.3 | <0.3 | <0.3 | <0.3 | <0.3 | <0.3 |

The only tissue showing significant differences between specific and nonspecific antibody is the tumor. All other tissues examined show approximately equal uptake between the specific and nonspecific antibodies. One possible exception is the lower blood levels for the nonspecific antibody, FA6. This indicates accelerated blood clearance of this antibody. However, the difference between the specific and nonspecific antibody in the tumor is greater than the difference in blood levels between the FA6 and BR96 antibodies.

The data in Table 7 also demonstrate that the percent of the dose present in a particular organ is constant regardless of the dose administered. This would therefore indicate there is quantitatively more antibody present at the tumor site when higher doses are administered. In addition, there are no apparent differences between the two tumor lines with respect to specific vs nonspecific uptake.

Table 7 also demonstrates that the F(ab')$_2$ was cleared from the animal at a much faster rate than either the IgG$_3$ or chimeric BR96. This could explain the reduction in efficacy of the fragment compared to the whole antibody therapy experiments. Any antitumor effects from the fragment must therefore be rapid and occur during the short time span prior to being cleared.

ChiBR96 localized at a comparable level to the IgG$_3$ BR96. Higher amounts were present only in the tumor compared to the control chimeric antibody. This suggests that any increase in efficacy of the chimeric antibody compared to the murine BR96 IgG$_3$ is due to the human constant region substitution. Of equal importance, the human constant region substitution does not appear to effect the ability of the chimeric antibody to localize to the tumor or adversely affect its biodistribution.

In summary, the IgG$_3$ and chimeric forms of BR96 are capable of specifically localizing to the tumor site. Moreover, both localization and therapeutic effects have been shown in these preliminary experiments at comparable doses. Indirect evidence of localization of the F(ab')$_2$ fragments was shown by the antitumor activity of the fragments in the therapy experiments. This activity must occur before 24 hours.

While we have presented particular embodiments of this invention herein, it is apparent that variations and modifications can be effected within the scope of the invention. Therefore, it will be appreciated that the scope of this invention is to be defined by the claims appended hereto rather than by the specific embodiments which have been presented herein by way of example.

We claim:

1. Murine monoclonal antibody BR96 produced by the hybridoma HB10036 as deposited with the ATCC.

2. Hybridoma HB 10036 as deposited with the ATCC.

3. An Fab, F(ab')$_2$ or Fv fragment of the antibody of claim 1.

4. A recombinant protein which is a murine/human chimeric antibody having (a) a variable region of monoclonal anitbody BR96 produced by hybridoma HB10036 and (b) a constant region of human origin.

5. An antibody or antigen binding fragment thereof that specifically binds to human carcinoma cells, said anitbody (1) characterized by internalization within the carcinoma cells with which it reacts, mediation of ADCC and CDC activity, and killing of said human carcinoma cells in the absence of host effector cells or complement and (2) having an antigen-binding region of murine monoclonal antibody BR96 produced by hybridoma ATCC No. HB10036 and a constant region of human origin.

6. An Fab, F(ab')$_2$ or Fv fragment of the antibody of claim 1.

7. Chimeric antibody Chi BR96 produced by the cell line deposited under the accession number HB 10460, said chimeric antibody having an antigen-binding region of murine monoclonal antibody BR96 produced by hybridoma ATCC No. HB10036 and a human IgG$_1$ constant region.

8. A cell line deposited under the accession number ATCC HB 10460.

9. An Fab, F(ab')$_2$ or Fv fragment of the antibody of claim 7.

10. A monoclonal antibody or antigen-binding fragment thereof that specifically binds to human carcinoma cells, wherein said monoclonal antibody and antigen-binding fragment have an antigen-binding region of murine monoclonal antibody BR96 produced by hybridoma ATCC No. 10036.

11. A monoclonal antibody of claim 10.

12. An antigen binding fragment of claim 10 selected from the group consisting of an Fab, F(ab')$_2$ and Fv fragment.

* * * * *

UNITED STATES PATENT AND TRADEMARK OFFICE
CERTIFICATE OF CORRECTION

PATENT NO. : 5,491,088

DATED : February 13, 1996

INVENTOR(S) : Hellstrom et al.

It is certified that error appears in the above-identified patent and that said Letters Patent is hereby corrected as shown below:

In [54] Title, delete "VARIABLE REGION OF MAB BR 96 WHICH BIND".

In [54] Title, delete "CARCIMONA" and insert --CARCINOMA--.

Column 16, line 59, delete "the" after the word "of".

Column 18, line 16, delete "detected" after the word "cells".

Column 21, line 10, delete "BR6 RA" and insert --BR96-RA--.

Column 23, line 51, delete "Of" and insert --of--.

Column 24, line 1, delete "syntheticglycoproteins" and insert --synthetic glycoproteins--.

Column 24, line 22, delete $Le^{11c}$" and insert --$Le^y$--.

Column 34, Claim 5, line 43, delete "hydridoma" and insert --hybridoma--.

Signed and Sealed this

Twenty-second Day of April, 1997

*Attest:*

*Attesting Officer*

BRUCE LEHMAN

*Commissioner of Patents and Trademarks*